(12) United States Patent
Arefieg

(10) Patent No.: US 9,357,961 B2
(45) Date of Patent: *Jun. 7, 2016

(54) DEVICE FOR ENABLING PATIENT SELF TESTING AND TREATMENT SELF-ADMINISTRATION AND SYSTEM USING THE DEVICE FOR MANAGING THE PATIENT'S HEALTH CARE

(71) Applicant: Thuban, Inc., Ridgefield, CT (US)

(72) Inventor: Rana J. Arefieg, Ridgefield, CT (US)

(73) Assignee: Thuban, Inc., Ridgefield, CT (US)

( * ) Notice: Subject to any disclaimer, the term of this patent is extended or adjusted under 35 U.S.C. 154(b) by 380 days.

This patent is subject to a terminal disclaimer.

(21) Appl. No.: 13/774,845

(22) Filed: Feb. 22, 2013

(65) Prior Publication Data

US 2014/0243635 A1    Aug. 28, 2014

(51) Int. Cl.
*A61B 5/157* (2006.01)
*A61B 5/00* (2006.01)
*A61B 5/145* (2006.01)
(Continued)

(52) U.S. Cl.
CPC .............. *A61B 5/157* (2013.01); *A61B 5/0002* (2013.01); *A61B 5/1411* (2013.01); *A61B 5/14532* (2013.01); *A61B 5/1519* (2013.01); *A61B 5/150022* (2013.01); *A61B 5/15113* (2013.01); *A61B 5/15117* (2013.01); *A61B 5/150328* (2013.01); *A61B 5/150358* (2013.01); *A61B 5/150412* (2013.01); *A61B 5/150854* (2013.01); *A61B 5/4839* (2013.01); *A61B 5/0004* (2013.01); *A61B 5/097* (2013.01); *A61B 5/15123* (2013.01);

(Continued)

(58) Field of Classification Search
CPC ...... A61B 5/14532; A61B 5/15; A61B 5/157; A61M 5/14244
See application file for complete search history.

(56) References Cited

U.S. PATENT DOCUMENTS

| 4,226,235 A | 10/1980 | Sarnoff et al. |
| 4,329,988 A | 5/1982 | Sarnoff et al. |

(Continued)

FOREIGN PATENT DOCUMENTS

EP    1102194    5/2001

OTHER PUBLICATIONS

Humapen Memoir Insulin Delivery Device User Manual, Eli Lilly & Company, 2006.

(Continued)

*Primary Examiner* — Catherine B Kuhlman
(74) *Attorney, Agent, or Firm* — David M. Quinlan, P.C.

(57) ABSTRACT

A portable unit comprises a sampling mechanism used by a patient to take a sample of a bodily fluid or tissue that can be tested for any property indicative of a medical condition of the patient, a microprocessor for determining a treatment for the condition based on a test of the sample, and an administration mechanism for administering the treatment based on the determination by the microprocessor. Operationally, the unit samples a bodily function, evaluates the sample, determines from stored protocols and criteria if treatment is required, and administers treatment. Two-way wireless communication between the unit and one or more remote networks enables numerous functionalities, including (i) collection and collation of medical information and records relating to multiple users of information stored by their units for access by healthcare providers, regulatory agencies, insurance carriers, pharmaceutical companies, and others, (ii) unit maintenance and resupply of consumables, and (iii) direct user-to-user communication.

28 Claims, 8 Drawing Sheets

(51) Int. Cl.
*A61B 5/15* (2006.01)
*A61B 5/151* (2006.01)
*A61B 5/097* (2006.01)

(52) U.S. Cl.
CPC . *A61B 2560/0266* (2013.01); *A61B 2562/0295* (2013.01)

(56) References Cited

U.S. PATENT DOCUMENTS

| | | | |
|---|---|---|---|
| 4,578,064 | A | 3/1986 | Sarnoff et al. |
| 4,731,726 | A | 3/1988 | Allen |
| 5,019,974 | A | 5/1991 | Beckers |
| 5,536,249 | A | 7/1996 | Castellano |
| 5,593,390 | A | 1/1997 | Castellano |
| 5,728,074 | A | 3/1998 | Castellano |
| 5,822,715 | A | 10/1998 | Worthington |
| 5,840,020 | A | 11/1998 | Heinonen |
| 5,925,021 | A | 7/1999 | Castellano et al. |
| 6,021,392 | A | 2/2000 | Lester et al. |
| 6,175,752 | B1 * | 1/2001 | Say ............ A61M 5/1723 128/903 |
| 6,192,891 | B1 | 2/2001 | Gravel et al. |
| 6,302,855 | B1 | 10/2001 | Lav et al. |
| 6,544,212 | B2 | 4/2003 | Galley et al. |
| 6,875,195 | B2 | 4/2005 | Choi |
| 6,906,802 | B2 | 6/2005 | Voelkel |
| 6,996,538 | B2 | 2/2006 | Lucas |
| 7,404,796 | B2 | 7/2008 | Ginsberg |
| 7,427,275 | B2 | 9/2008 | DeRuntz et al. |
| 7,534,230 | B2 | 5/2009 | Follman et al. |
| 7,591,801 | B2 * | 9/2009 | Brauker et al. ............ 604/161 |
| 7,737,858 | B2 | 6/2010 | Matiyaho |
| 7,871,393 | B2 | 1/2011 | Monroe |
| 7,988,630 | B1 | 8/2011 | Osorio et al. |
| 8,044,778 | B2 | 10/2011 | Monroe |
| 8,149,111 | B2 | 4/2012 | Monroe et al. |
| 8,206,340 | B2 | 6/2012 | Arefieg |
| 8,361,026 | B2 | 1/2013 | Edwards et al. |
| 8,366,682 | B2 | 2/2013 | Wyrick |
| 2002/0013522 | A1 | 1/2002 | Lav et al. |
| 2002/0016719 | A1 * | 2/2002 | Nemeth et al. ............ 705/2 |
| 2005/0075954 | A1 | 4/2005 | Matsumoto et al. |
| 2006/0135874 | A1 * | 6/2006 | Peng ............ 600/509 |
| 2006/0173406 | A1 | 8/2006 | Hayes et al. |
| 2007/0055586 | A1 | 3/2007 | Lucas |
| 2007/0066938 | A1 * | 3/2007 | Iio ............ A61B 5/1411 604/152 |
| 2007/0197968 | A1 | 8/2007 | Pongpairochana et al. |
| 2008/0119705 | A1 | 5/2008 | Patel et al. |
| 2008/0269673 | A1 | 10/2008 | Butoi et al. |
| 2008/0306434 | A1 | 12/2008 | Dobbles et al. |
| 2009/0105570 | A1 | 4/2009 | Sloan et al. |
| 2009/0137957 | A1 | 5/2009 | Wagener |
| 2009/0138207 | A1 | 5/2009 | Cosentino et al. |
| 2010/0010330 | A1 | 1/2010 | Rankers et al. |
| 2010/0016700 | A1 | 1/2010 | Sieh et al. |
| 2010/0090004 | A1 | 4/2010 | Sands et al. |
| 2010/0141457 | A1 | 6/2010 | Wass et al. |
| 2010/0256593 | A1 | 10/2010 | Yodfat et al. |
| 2011/0082711 | A1 | 4/2011 | Poeze et al. |
| 2011/0184264 | A1 | 7/2011 | Galasso et al. |
| 2011/0282173 | A1 | 11/2011 | Fonduca et al. |
| 2011/0320130 | A1 | 12/2011 | Valdes et al. |
| 2012/0046606 | A1 | 2/2012 | Arefieg |
| 2012/0047049 | A1 | 2/2012 | Cadiz |
| 2012/0173287 | A1 | 7/2012 | Cowand |
| 2012/0203566 | A1 | 8/2012 | Kidd et al. |
| 2012/0238853 | A1 | 9/2012 | Arefieg |
| 2012/0278228 | A1 | 11/2012 | Rubinstein |
| 2014/0142507 | A1 * | 5/2014 | Armes ............ A61M 5/3287 604/112 |

OTHER PUBLICATIONS

"A New Era in Blood Glucose Monitoring Begins: The Accu-Chek Mobile System," Trade News, Vienna, Austria, Roche Diabetes Care, Sep. 30, 2009.

Walsh, J., "Concept 2: The Smart Insulin Pen," www.diabetesnet.com/diabetes_technology/smart_pen.php (last visited Mar. 25, 2010).

International Search Report and Written Opinion, dated Oct. 31, 2011 in PCT Appln. No. PCT/US11/01349.

Thomas, Katie, "Tiny Lifesaver for a Growing Worry," New York Times, Sep. 8, 2012, pp. B1-B2.

Thomas, Seth, "Tiny Lifesaver for a Growing Worry," New York Times, Sep. 8, 2012, pp. B1-B2.

International Search Report and Written Opinion, dated Mar. 20, 2015, in PCT Appln. No. PCTUS14/16648.

* cited by examiner

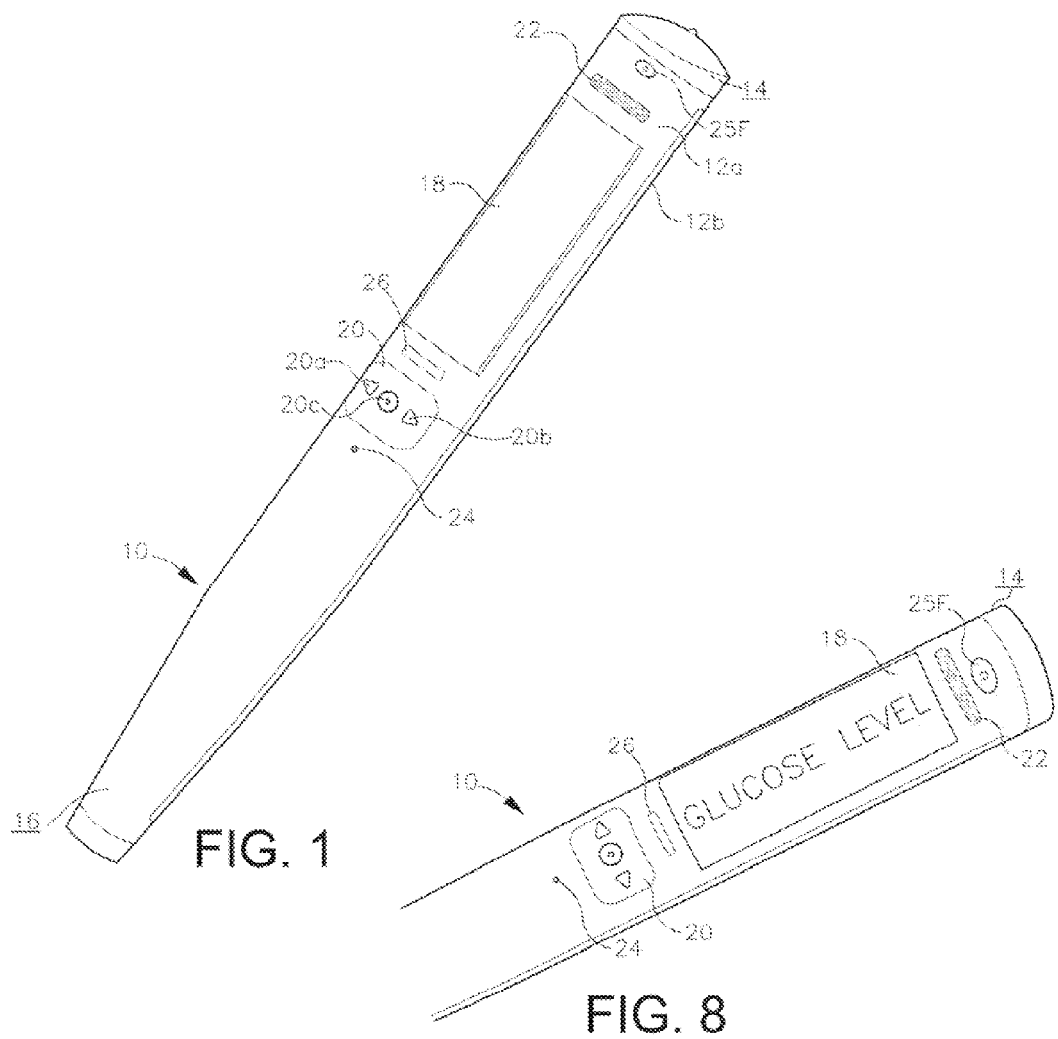
FIG. 1
FIG. 8
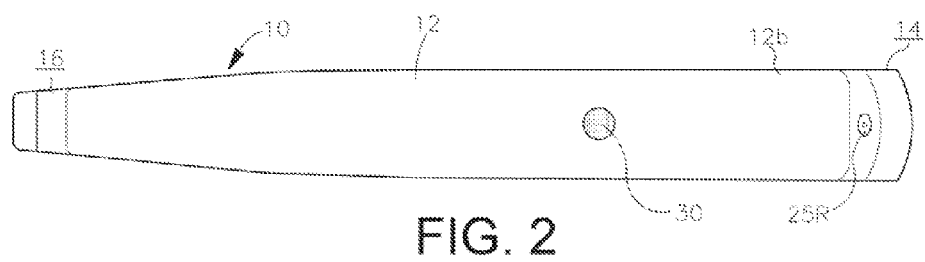
FIG. 2

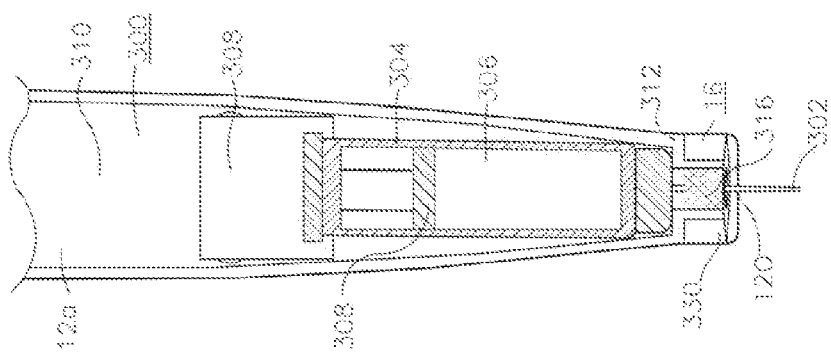
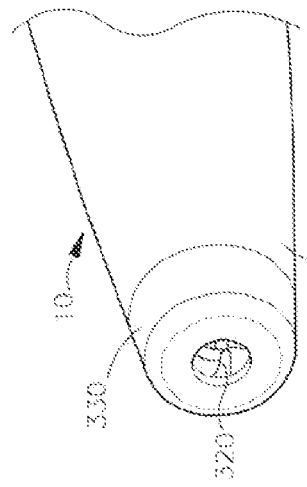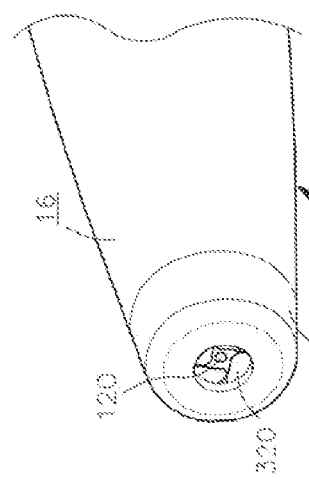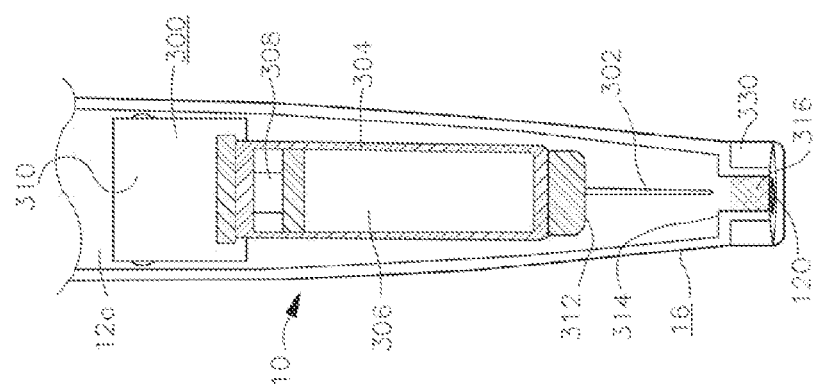

DEVICE FOR ENABLING PATIENT SELF TESTING AND TREATMENT SELF-ADMINISTRATION AND SYSTEM USING THE DEVICE FOR MANAGING THE PATIENT'S HEALTH CARE

BACKGROUND OF THE INVENTION

1. Field of the Invention

The present invention relates to monitoring a patient's compliance with treatment protocols relating to a medical condition, and more particularly, to a device for enabling self-testing and medication self-administration and to a system for communicating with the device to assist in management of the medical condition.

2. Description of Related Art

U.S. Pat. No. 8,206,340 ("the '340 patent") describes a first generation device with multiple functionalities that facilitate patient self-management of medical conditions such as diabetes. For example, the device includes a blood glucose monitoring function and an insulin injection mechanism integrated into a single unit that fits in a handbag or pocket. A microprocessor in the unit automatically calculates an insulin dosage based on a blood glucose level detected using the unit and controls the insulin injection mechanism to administer the calculated dosage. The device can also download and store treatment protocols appropriate to particular patients and monitor and report patient compliance with the protocols by interfacing with a healthcare provider for that patient. Information exchanges between a healthcare provider and the device can be performed by remote data transfer via cellular telephony, wireless cloud-based communication, or the like. Another feature automatically notifies an emergency service provider if the unit senses that the patient has failed to administer an insulin dosage within a predetermined time after the unit determines that one is necessary.

The device described in the '340 patent includes the above-mentioned features, as well as many other many useful functionalities that improve over prior art devices directed to combining blood glucose monitoring and insulin injection functions into a single unit. Examples of such prior art devices are described in U.S. Pat. No. 5,728,074 and U.S. Patent Publ. No. 2011/0282173. The '340 patent is incorporated by reference into the present description as if set forth in full herein, and the present invention is capable of performing all of the functions of the device and the systems with which it interacts as described in the '340 patent. The manner in which the unit, systems, and methods described herein improve over various features of the prior art in general, and over the non-prior art '340 patent will be apparent from the description below of preferred embodiments of the present invention.

SUMMARY OF THE INVENTION

It is an object of the present invention to improve various constructional aspects of the integrated device described in U.S. Pat. No. 8,206,340 to enhance the utility thereof and further facilitate patient monitoring and medication administration of such an integrated unit.

It is another object of the present invention to improve and expand on the functionalities of the unit described in the '340 patent, and the methods of using it for patient care and for interacting with other systems, so as further to assist patients in managing and treating various medical conditions, and to enable healthcare providers, medical supply manufacturers and distributors, and regulatory agencies in performing and coordinating their various functions to ensure that patients receive optimum medical care.

One more specific object of the invention is to embody one of its core concepts into a unit that includes in combination: (i) a sampling mechanism for taking from a patient a sample that cart be tested for a property indicative of a medical condition of the patient (ii) circuitry such as a microprocessor for determining a treatment for the condition based on a test of the sample, and (iii) an administration mechanism for administering the treatment based at least in the first instance on the determination by the circuitry (although in another aspect of the unit a user can override the recommended treatment). A separate but related core concept resides in using such a unit to sample a bodily function of an organism (human or animal), evaluate the sample, determine from stored protocols and criteria if treatment is required based on the evaluation, and administer treatment.

Another object of the unit is to enhance the functionality of such a unit with the features described herein to enhance healthcare in myriad ways by using hardware and software implementations that enable one or more of the following additional functions: (a) two-way communication via one or more communication platforms connecting the unit and a healthcare provider or other information source to enhance and optimize the quality of medical care rendered to the patient using the unit, (b) using the forgoing communication capability to enable a healthcare provider to download treatment protocols and updates of same to the unit and enable the unit to upload to the healthcare provider information on patient compliance with the treatment protocols, (c) automatically notify emergency services or responders if the unit detects that the patient is in danger, with the optional capability of also providing the patient's location, (d) communication between the unit and a user, including a patient, physicians, other healthcare providers, etc., via voice recognition (user-to-unit), handwriting recognition (user-to-unit), visual displays via a display on the unit, and any other communication device or platform for user/unit communications, (e) transfer to a central system for collection and collation of medical information and records relating to multiple users of information stored by a unit, and (f) interconnection with an ecosystem that provides a venue for one or more of unit maintenance and resupply of consumables used by the unit, direct user-to-user communication, access by regulatory agencies, insurance carriers, pharmaceutical companies, public health agencies and others.

In accordance with one variation, the administration mechanism of the unit described above can be adapted to administer two or more medications. In an advantageous implementation of this variation, different medications are administered by interchangeable administration modules.

An additional aspect of the invention the unit includes control circuitry and at least one administration module under the control of circuitry such as a microprocessor, but omits or disables the sampling mechanism of the unit described above.

This Summary is provided to introduce a selection of concepts in a simplified form that are further described below in the Detailed Description. This Summary is not intended necessarily to identify key or essential features of the claimed subject matter, nor is it intended to be used in determining the scope of the claimed subject matter

BRIEF DESCRIPTION OF THE DRAWINGS

The objects of the invention will be better understood from the detailed description of its preferred embodiments which follows below, when taken in conjunction with the accompanying drawings, in which like numerals and letters refer to like features throughout. The following is a brief identification of the drawing figures used in the accompanying detailed description.

FIG. 1 is an isometric view of the front side of an integrated unit used to sample bodily fluids and administer medications, which further permits exchange of information with other systems and databases, according to an embodiment of the present invention.

FIG. 2 is a plan view of the rear side of the unit in FIG. 1.

FIG. 8 shows the LCD display of the unit in FIG. 1 displaying the results of the unit's analysis of a sample of bodily fluid after collection thereof in accordance with one aspect of the present invention.

FIGS. 9 and 10 schematically illustrate the construction and operation of the administration module and its associated hypodermic needle for administering medication based on the analysis of the bodily fluid collected by the sampling module in accordance with the operation illustrated in FIGS. 4 to 7.

FIGS. 11 and 12 are detail views of a second end of the unit in FIG. 1, with FIG. 11 illustrating a closure covering an aperture for the hypodermic needle shown in FIGS. 9 and 10 and FIG. 12 showing the closure in a position covering the aperture.

FIG. 14, comprising

One skilled in the art will readily understand that the drawings are not strictly to scale, but nevertheless will find them sufficient, when taken with the detailed descriptions of preferred embodiments that follow, to make and use the present invention.

DETAILED DESCRIPTION OF PREFERRED EMBODIMENTS

The embodiment of the invention chosen for illustrative purposes is an integrated blood glucose monitor and insulin pen unit that can collect a blood sample from a patient, analyze the glucose level in the sample, calculate an insulin dosage based on the insulin level, if appropriate, and administer the calculated dosage. In essence, the described unit can perform all of the functions of the device described in U.S. Pat. No. 8,206,340 (which is incorporated herein in full by reference). However, it will become apparent as the present description proceeds that the unit has greatly enhanced functionality and improved constructional features not suggested by the '340 patent. The description below first describes constructional details and the operation of one embodiment of a unit with features that exemplify aspects of the present invention. Following that, there is a description of various exemplary functionalities that can be effected by a unit embodying the constructional features. Finally, there is a description of numerous other applications of a unit, according to the present invention for that enable monitoring and treating a variety of medical conditions.

Exemplary Constructional Features of the Unit

Figure 3:
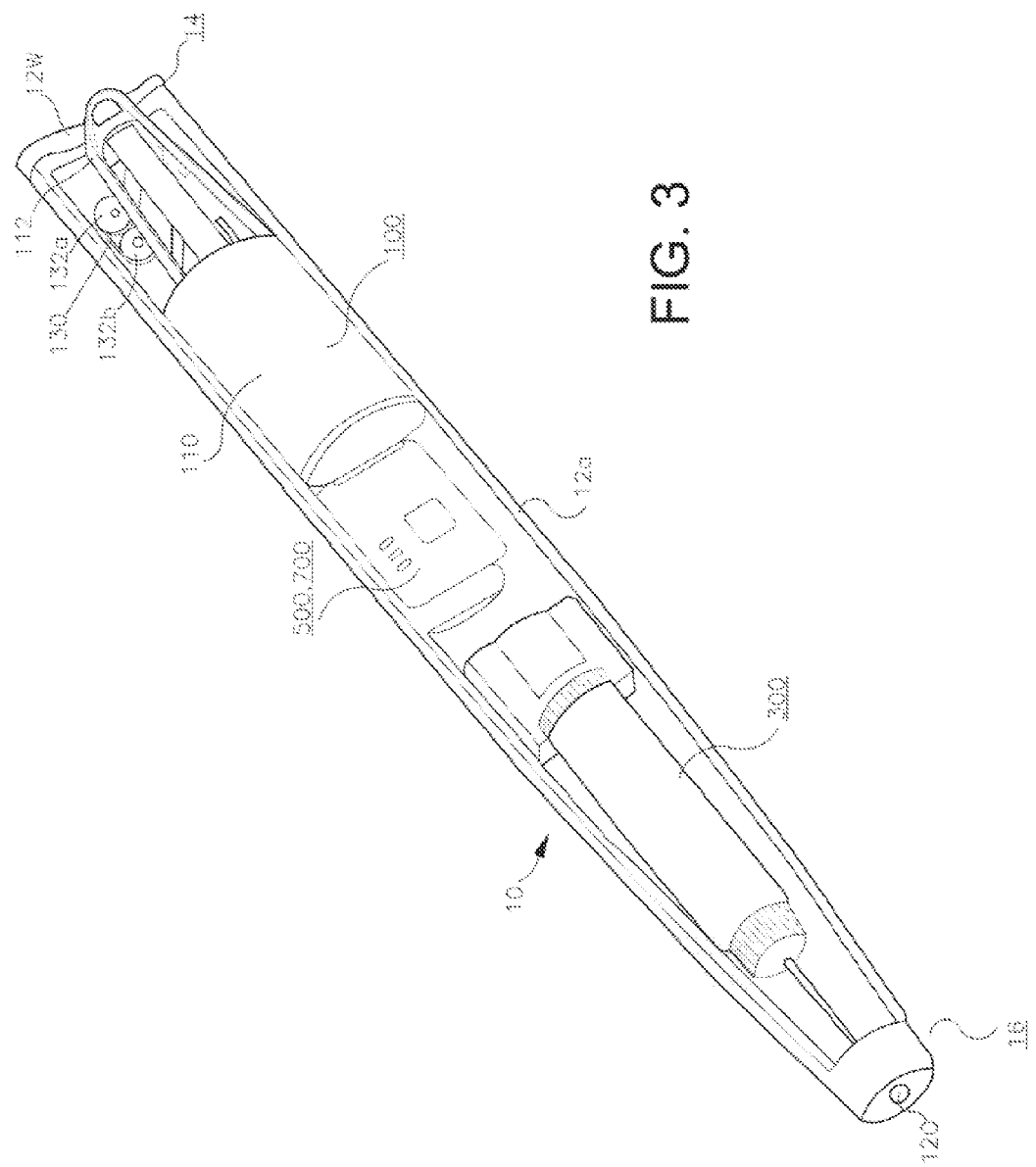
FIG. 3 shows the unit in FIG. 1 with the rear half of its housing removed to show schematically various modules included in the unit.

FIGS. 1 to 3 show basic constructional features of an integrated unit 10 in accordance with one embodiment of the present invention. FIG. 1 is an isometric view of the front side of an integrated unit 10 used to sample bodily fluids and administer medications. The unit 10 includes a housing 12, comprising a front part 12a and a rear cover 12b, that encloses its functional components, which are described in detail below. The unit has a first top end 14 at which a blood sample can be taken, as described further below, and a second bottom end 16 at which a hypodermic needle can extend for administering insulin in a manner also described further below. (In describing embodiments of the invention, terms indicating direction or orientation, such as "front," "rear," "right," "left," "top," "bottom," etc., may be used to facilitate the description. They do not imply that the invention is limited to a particular orientation of the unit).

The unit 10 includes various user interface components. These include a display 18 for displaying to the user various prompts and informational messages as described below. The display 18 is preferably an LCD display, although other display constructions are possible and the invention is not limited to any particular type of display. A touch device 20 comprises another user interface component. The touch device 20 includes directional arrows 20a and 20b, and an input button 20c. In one form of the unit 10, the touch device 20 is used in conjunction with the LCD display 18 to operate the unit. For example, a menu may be displayed on the LCD display and the user can use the arrows 20a and 20b to scroll through the menu until reaching a desired menu item, at which time the user touches the input button 20c to choose that menu item. In an alternate embodiment the display itself can enable touch screen input, permitting the user to choose selected functions and operations directly on the display, thus eliminating the need for a separate input touch device. Other user interface components include a speaker 22 and a microphone 24. It is understood that the term "speaker" encompasses an optional headset that could be plugged into a port (not shown) in the unit. The various functions of the speaker and microphone are covered in detail by the description that follows below. The user interface also comprises front and rear cameras 25F and 25R (see FIG. 3) under the control of the user via the touch device 20. The user can operate the cameras simultaneously, or in still or video mode. The user interface can further include a vibration device (not shown) that provides tactile signals to a user. This option enables users who are hearing and/or vision impaired to take advantage of the unit's capabilities. It is particularly useful if the unit is configured for managing medical conditions (such as diabetes) that can cause vision impairment. The unit further includes a USB port 26 that permits attachment of a standard USB cable for purposes described further below. It is preferable to use a mini- or micro-size USB connection consistent with the general goal of miniaturizing the unit to the greatest possible extent.

As seen in FIG. 1, the unit 10 has an elongated configuration that is not only attractive, but enables its various mechanical and electronic components to be contained in a compact device easily carried in a pocket or handbag/purse. In addition the unit tapers slightly toward its bottom end 16 to provide a tactile and visual indication to the user regarding the end of the unit to use to administer an injection. A preferred configuration will typically be generally circular in cross section with a diameter of about 0.75" to 1.5" and will be about 4" to 6" long, although other configurations and dimensions can be used within the broadest scope of the invention. FIG. 2 shows the reverse or back side of the housing 12 with a rear cover release 30. The housing 12 is molded in two parts that fit together along a longitudinal seam, and the rear cover release is spring loaded into a position that holds the two housing halves together. Pressing the rear cover release 30 against the spring force allows the user to remove a rear cover half 12b of the housing 12 and access the interior of the unit. Details of the spring latch formed by the rear cover release are omitted here since construction of a latching arrangement consistent with the objects and uses of the unit 10 as described herein is well within the ability of those skilled in the art. It will also be clear that the invention is not limited to any particular configuration or dimensions. For example, one skilled in the art may chose to arrange the internal components of the unit discussed below in a manner that makes it preferable to use a different configuration or a different size housing.

FIG. 3 shows the interior of the unit 10 from the rear with the rear cover 12b removed. The unit includes a sampling module 100, an administration module 300, and a control module 500 that provides overall control of the unit in accordance with inputs from the user, the sampling module 100 and the administration module 300. A battery (not shown) provides electrical power to those components requiring it (the modules, the display, the speaker, etc.), and is preferably a lithium polymer rechargeable battery, although other types of battery can be used within the scope of the invention. The control module 500 preferably comprises an integrated circuit that includes a microprocessor for effecting overall control of the unit and its various functionalities. In a fashion familiar to those skilled in the art, the microprocessor incorporates a read-only memory ROM storing an operating system and a random access working memory RAM enabling the microprocessor to execute programs stored in the ROM. These programs include algorithms that use inputs to the control module to determine medication dosages and other outputs that enable functionalities of the unit discussed herein further below. For example, if the unit is configured for diabetes management, the microprocessor would include programs that enable the unit to manage a patient's symptoms and perform the other functions and methods described in U.S. Pat. No. 8,206,340.

The control module 500 serves several overall purposes in achieving objects of the invention. One purpose is to accept inputs from various sensors within the unit and from user interface components (such as the touch device 20 and the microphone 24), and provide operating outputs to the sampling module 100, the administration module 300, and user interface components (such as the display 18 and the speaker 22, or a vibration device). The control module 500 also accepts inputs from and provides outputs to the USB port 26 for various purposes described in the course of the following description. The control module further includes a memory for storing data. Many of the uses and functionalities provided by the unit 10 are described in U.S. Pat. No. 8,206,340, and the unit described herein is capable of providing all of those functionalities, as well as the many others described more fully herein.

The unit 10 further includes a communications module 700 for enabling communications between the unit 10 and systems and components external to the unit. The communications module can comprise the software and firmware for enabling communication with systems external to the unit, via either a wired connection or a wireless connection such as Wi-Fi or cellular telephony. In that regard, the communications module would include at least one of a GPS, cell phone, Bluetooth, and Wi-Fi transceiver. Certain components of the communications module can be incorporated in the integrated circuit that also includes control module components discussed above, this commonality being indicated by associating both of the reference numerals 500 and 700 with the integrated circuit and associated electronics illustrated schematically in FIG. 3. These various components enabling communications with a system external to the unit are of known construction and operation, and those skilled in the art will thus be able to incorporate them into the unit 10 without further explanation. Functionalities of the communications module are described below in more detail in connection with the operation and control of the unit 10.

It will be further understood that the term "module" as used herein does not necessarily denote a physically separate, unitary component. The term when applied to a constructional feature is to be understood to mean a collection of structural components that can be more readily understood in the context of the related functions they perform together. When applied to software or firmware, or information, the term is to be understood in a broad sense as information in the form of executable instructions, storage locations, electronic circuitry, etc., that may be found in various locations in the storage media on which they reside. Therefore, unless specifically stated, reference to a "module" is solely for convenience of description, in that certain functionalities of the unit 10 and the systems with which it can communicate, are more readily discussed by grouping them together to aid understanding how they achieve the purposes and objects of the subject matter claimed herein. Any parts of the unit 10 and its various modules discussed herein that are constructed as separate, unitary components are specifically stated as such.

The Sampling Module 100

Figure 4:
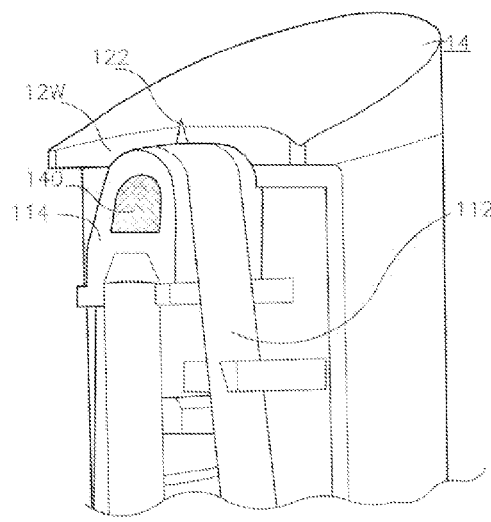
FIGS. 4 to 6 taken together schematically illustrate the construction of a bodily fluid sampling module in the unit in FIG. 1, with FIGS. 4 and 5 being partial isometric views of the sampling module respectively illustrating extended and retracted positions of a lancet and FIG. 6 being a cross-sectional view showing a lancet, operating mechanism.
Figure 5:
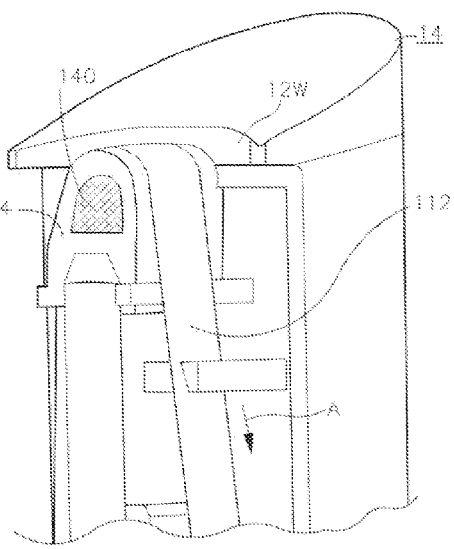
Figure 6:
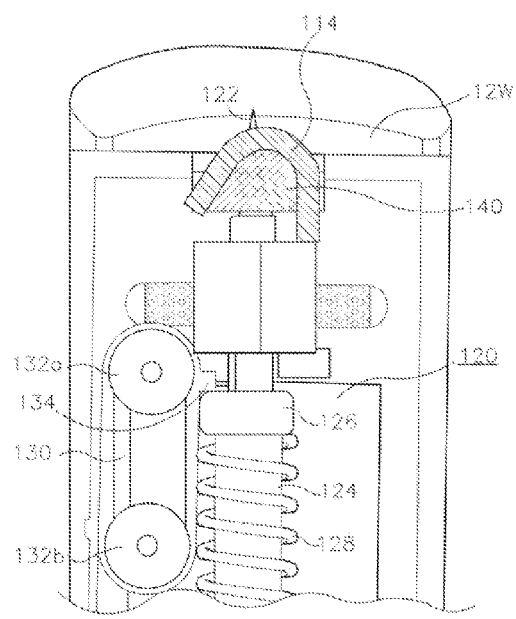

FIGS. 4 to 6 comprise enlarged views of the first top end 14 of the unit 10, with the rear cover 12b removed to show details of the construction and operation of the sampling module 100. It will be understood that the depictions in these figures are highly schematic, but that taken with the rest of the description herein they are sufficient to enable one of ordinary skill in the art to construct a sampling module with the features and functions described herein. Generally, the sampling module includes a housing 110 (see FIG. 3) in which is disposed a first supply reel (not shown) around which one end of a test strip 112 (omitted from FIG. 6 for clarity) is wound and a second take-up reel (not shown) around which the other end of the test strip is wound. As seen in the figures (including FIG. 3), the test strip 112 extends from the housing 110, over a slide support 114, and back into the housing 110. A micromotor (not shown) in the housing 110 drives the take-up real to draw the test strip 112 from the supply reel and over the slide support 114 in the direction of the arrow A in FIG. 5. The micromotor is preferably a step motor that responds to pulses from the control module 500 to advance the test strip a predetermined distance set by the relevant program in the microprocessor. The supply reel would typically be spring-loaded to resist rotation, thus maintaining the test strip in tension as it is advanced from the supply reel by rotation of the take-up reel.

The slide support 114 positions the test strip 112 to extend just outside a window 12W at the first top end 14 of the unit. As shown in more detail in FIG. 7, a lid 12L (omitted from FIGS. 4 to 6 for clarity) is mounted to the unit end 14 for rotation between an open test position (shown in these figures) that exposes the test strip 112 and a dosed stowed position. When the user rotates the lid 12L to the open test position, it exposes the test strip 112 through the window 12W to enable the user to place a bodily fluid sample (In the present example, a drop of the user's blood) on the test strip. FIG. 6 shows the sampling module with the test strip removed to better depict a lancet mechanism 120 for drawing a blood sample. The lancet mechanism includes a lancet 122 with a razor-sharp point at the end of a lancet shaft 124 extending into the unit. The lancet 122 can advantageously be coated with Teflon® polymer and/or a suitable antimicrobial coating. A flange 128 surrounds the shaft and provides a bearing surface for a coil spring 128 that forcefully and rapidly drives the lancet upward though the opening 12W (see FIGS. 5 and 6) to pierce a location on the user's skin placed over the window 12L. A lancet arming mechanism includes an endless retracting belt 130 that extends around two pulleys 132a and 132b. A micromotor (not shown) rotates the shaft of one of the pulleys 132a, 132b to move an arming tab 134 that bears against the top of the flange 126. When the motor rotates a pulley 132a, 132b clockwise (as seen in FIG. 6), the tab 134 pushes the flange 126 downward to compress the spring for arming the lancet mechanism. When the lancet flange 126 reaches a predetermined position, a spring-loaded latch (not shown) engages the flange 126 to hold the lancet mechanism in its armed condition with the spring 128 compressed. A latch solenoid (not shown) is energized in accordance with the operation of the unit described below to release the latch and permit the spring 128 to propel the lancet 122 quickly upward (as seen in FIGS. 4 and 5).

Figure 7:
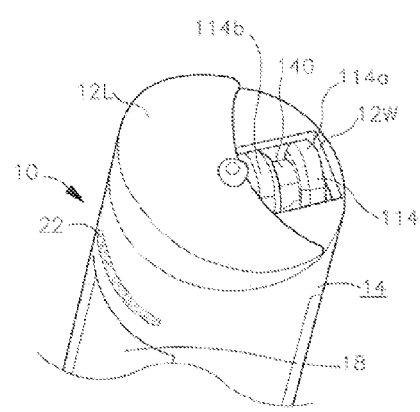
FIG. 7 is a detail view of the unit in FIG. 1 illustrating the manner in which a lid at a first end of the unit is rotatably mounted to expose the sampling unit for permitting a user to take a blood sample.

FIG. 7 is a view from outside the unit 10 at the first end 14, with the lid 12L rotated into the open position to expose the window 12W. In this view, the test strip 112 is omitted to illustrate that the slide support 114 includes two spaced apart positioning rails 114a and 114b with a slot between them through which the lancet extends when propelled upward by the spring 128. The rails 114a and 114b are spaced apart a distance that matches the width of the test strip 112, so that the test strip's opposing lateral edges contact with the inner surfaces of the rails. This captures the test strip 112 between the rails to position it laterally as it is drawn over the slide support. The sampling module can further include guides extending between the housing 110 and the slide support 114 to assist in maintaining the proper position of the test strip, and sensors may be provided as well to provide a signal to the microprocessor that will trigger an alert (audible or otherwise) to the user that the test strip is out of position. Further, as seen most clearly in FIG. 6, the sampling module includes a lancet disinfectant tablet 140 through which the lancet 122 travels before and after it pierces the user's skin. The tablet 140 comprises a replaceable pad made of a suitable material that sterilizes the lancet 122 as it passes through the tablet. The tablet can have any suitable construction or composition that achieves its purpose. A suitable tablet could be made of a surgical sponge material impregnated with a liquid disinfectant/fungicide, and optionally covered by silicone rubber to retard evaporation. Broadly speaking, the tablet 140 comprises means for disinfecting the lancet and can take any form suitable for that purpose. Some examples of equivalent structure are a rubber or plastic container that holds a liquid disinfectant, (which in the present context is defined as any substance that kills microbes, fungi, protozoa, and other infectious agents), and is made of a material that reseals after the lancet 122 is withdrawn. Other examples are a solid material that itself disinfects the lancet as the lancet passes through it, and a device that emits radiation in infrared and/or ultraviolet wavelengths or other type of bactericidal/fungicidal radiation. If the disinfectant is a separate substance, it can be iodine or alcohol or other liquid disinfectants, either alone or in combination.

In a preferred embodiment, various components of the sampling module 100 form a unitary structure that can be removed and replaced when the test strip supply in the housing has been completely used. For example, it is contemplated that in one embodiment the sampling module, including the housing 110, will include a sufficient length test strip to last for several days to a week or more, after which the entire module is discarded and replaced with a new sampling module with a fresh test strip. In a particularly preferred embodiment, motors used by the various components and the solenoid-controlled lancet latch would remain in the unit, and the unit and sampling modules would include suitable mechanical interfaces for the motors and solenoid that form a permanent part of the unit. In addition, the tablet 140 could be separately replaceable independently of the replaceable sampling module by providing a shaped opening such as that shown in FIG. 6 for the tablet.

After the sampling module 100 determines the blood glucose level, it sends a data signal to inform the control unit 500, in response to which the control unit causes the LCD display 18 to show the test results to the user, as illustrated in FIG. 8. A more detailed description of a complete test/administration cycle is described further below after the following detailed description of the construction of the administration module 300.

The Administration Module 300

FIGS. 9 and 10 depict the unit 10 with the rear cover 12b removed to illustrate additional details relating to the construction and operation of the administration sampling module 300, (See FIG. 3 also). The administration module comprises an injection mechanism powered by two micromotors (not shown) that drive a hypodermic needle 302 downward (as seen in FIGS. 9 and 10) through an opening 12O in the second end of the unit 10, to be described in more detail just below. The needle 302 is mounted to a syringe assembly 304 that includes a chamber 306 for medication (insulin in this instance) that is in fluid communication with the hypodermic needle 302. A plunger 308 moves downward (as seen in FIGS. 9 and 10) to force the medication from the chamber 306 through the needle 302 in a conventional fashion. In the present embodiment, a module housing 310 includes one or more micromotors (not shown) that operate the administration module. Typically, there will be two motors controlled in sequence by the unit microprocessor, with the first motor operating a suitable mechanical linkage or other mechanism (not shown) for moving the administration module 300 bodily downward (as seen in FIGS. 9 and 10) until the chamber terminal end 312 reaches a shoulder 314 within the unit and the needle 302 extends externally from the unit's bottom end through an opening 12O. At that time, a second micromotor within the housing 310 operates the plunger 308 to administer a dosage of the medication in the chamber 306.

The unit further includes a needle disinfectant tablet 316 that fits in a recess behind, the opening 12O through which the needle 302 travels before and after it pierces the user's skin. The needle tablet 316 comprises a replaceable pad made of a suitable material as described above in connection with the lancet disinfectant tablet. It serves the same purposes as the lancet disinfectant tablet 140 and can have any of the constructions and compositions discussed in connection with the tablet 140. In that regard, the needle tablet 316 comprises means for disinfecting the needle and can take any form and have any property suitable for that purpose, and in particular, any of the forms, properties, and equivalent structures discussed in connection with the tablet 140. In a preferred embodiment, the syringe assembly 304 can be removed and replaced when the medication is depleted and replaced with a new syringe assembly having a fresh supply of medication. In addition, the tablet 316 could be separately replaceable independently of the replaceable syringe assembly.

FIGS. 11 and 12 are detailed views of the bottom second end 16 of the unit 10 showing an iris-like closure 320 similar to a camera aperture mechanism for covering the opening 12O except, for those times when an injection is to be administered. FIG. 12 shows the closure 320 in its open position, exposing the opening 12O to permit passage therethrough of the hypodermic needle 302. A preferred embodiment, a medication administration cycle is initiated when the user manually turns an actuating ring 330 encircling the unit's second end to a position that opens the iris closure 320. This triggers a sensor to indicate to the microprocessor that the opening 12O is exposed, at which time the microprocessor initiates an administration cycle in accordance with the particular protocol under which the unit is operating. The description of a complete test/administration cycle that follows includes additional details concerning the operation of the administration module 300.

Operation and Control of the Unit

System Components

Figure 13:
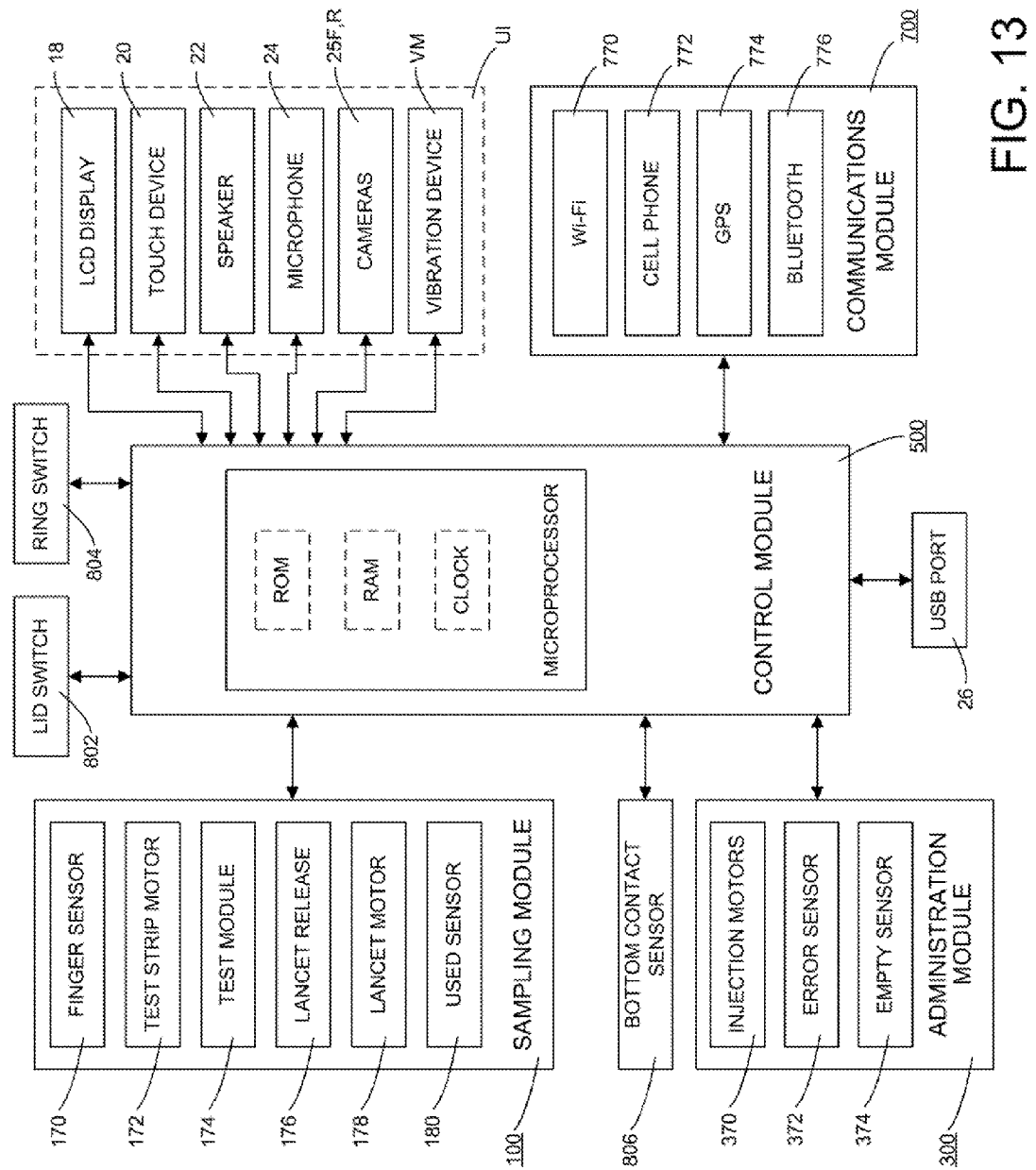
FIG. 13 is a simplified block diagram showing representative system components of the unit in FIG. 1 in accordance with the present embodiment, of the invention.

FIG. 13 illustrates schematically various system components and the manner in which they cooperate to operate the unit and carry out the various functionalities discussed herein. As already noted, the unit 10 is under the overall control of a microprocessor that is part of the control module 500. As described above, the microprocessor comprises a read-only memory ROM storing an operating system and executable programs that use algorithms and data provided to the unit to determine medication dosages and other parameters useful in managing a patient's medical condition, and that control the operation of the various other components of the unit described just below. The microprocessor also includes a random access working memory RAM to enable the microprocessor to execute programs stored in the ROM. Further, the microprocessor includes a clock that, in a conventional fashion, provides the timing pulses necessary for the microprocessor to perform its control functions.

In the present embodiment the unit 10 is adapted for use by a patient with diabetes to manage the symptoms of his or her condition in a convenient and intuitive manner. To that end, the sampling module 100 includes a finger sensor 170 that senses when a user's finger is in contact with the test strip 112 exposed through the window 12W in the top end 14 of the cover 12. In a preferred embodiment the linger sensor 170 detects a change in capacitance caused by contact of the sees finger (or other body part) with the test strip 112 and slide support 114 through the window 12W, although the presence of the user's finger can be sensed by other means, such as by using a mechanical sensing mechanism responsive to pressure by the user. The sensor 170 is electrically connected to the control module and the change in capacitance is interpreted by the microprocessor to indicate that a user's finger is in position to have a blood sample taken using the lancet 122. A test strip micromotor 172 in the sampling module housing 110 drives a take-up reel to draw the portion of the test strip containing the blood sample into the housing, where a test module 174 operates in accordance with known principles to determine the glucose level in the blood sample, and communicates the test results to the microprocessor. Advancing the test strip portion with the blood sample into the housing 110 brings a fresh portion of the strip 112 into position for accepting a new blood sample in a subsequent testing cycle. The details of the glucose level testing do not form a part of the present invention, and are well known to those skilled in the art. U.S. Pat. No. 5,728,074 describes various ways of performing such testing and obtaining a corresponding electrical signal. Any of those techniques, or variations thereof, can be used in performing blood glucose testing with the unit 10, and those portions of U.S. Pat. No. 5,728,074 describing such testing are incorporated by reference as if set out in full herein.

The blood sample is automatically taken by the lancet 122 while the user's finger is on the test strip. The lancet is held in a retracted, armed position against the force of the spring 128 (FIG. 6) by a latch. The latch is released by a signal from the microprocessor to a solenoid-actuated latch release 176 so that the lancet 122 will prick the user's finger (or other location) and draw the blood sample. A lancet micromotor 178 retracts the lancet against the force of the spring 128 as discussed above to return it to the retracted position where it re-engages the latch to lock the lancet in its armed condition, ready for taking the next blood sample. Thereafter, the motor returns the arming tab 134 to a waiting position (the position shown in FIG. 6) to await the next sampling cycle. The sampling module further includes a sensor 180 that determines when the test strip is nearly used up, and sends a corresponding signal indicating same to the control module.

The administration module 300 includes injection motors 370 that operate the administration module 300 to administer an injection as discussed above. The administration module further includes an error sensor 372 that ensures that the proper medication dosage is administered. The error sensor has built-in redundancy, in that it provides two signals to the control module 500. The first signal is generated by an encoder integrated into the injection motor 370 to provide a signal indicative of the amount of rotation of the motor shaft, and thus provide a real-time indication of the amount of insulin being injected as the injection motor rotates. The second signal is generated by an infrared defector that generates a signal based on detecting the actual location of the injection plunger as it moves in the hypodermic syringe, and thus provides a parallel, second real-time indication of the amount of insulin being injected. The microprocessor compares these two signals, and if they indicate injection volumes that differ by more than a predetermined amount, the microprocessor generates an error signal that halts the injection process and provides an error message to the user. Since the insulin dosage must be precisely controlled, the predetermined amount of variation between the two signals is typically small. For example, a suitable limit on the amount of variation between the signals is no more than 5%, with the limit on the variation most preferably being no greater than about 2%. The administration module also includes an empty sensor 374 that determines when the medication chamber 306 is nearly empty, and sends a corresponding signal indicating same to the control module.

The unit 10 further includes a lid switch 802 that senses when the lid 12L has been moved to its open test position (FIG. 5) and sends a corresponding signal indicating same to the control module. The lid switch can be implemented in any suitable fashion, and typically comprises a pair of electrical contacts that are brought into juxtaposition when the lid 12L is in the yen position shown in FIG. 5. The unit also includes a ring switch 804 that senses when the actuating ring 330 has been turned a sufficient amount to expose the needle opening 12O (FIG. 12) and sends a corresponding start signal to the control module indicating that an medication administration cycle has been enabled. The unit also includes a bottom end proximity sensor 806 similar in operation to the finger sensor 170 that is used by the sampling module 100. That is, the bottom end sensor is mounted within the unit 10 at the second bottom end 16 and detects a change in capacitance caused by contact of a body part of the user with the injection site on the unit (that is, the bottom end 16). The sensor 806 is electrically connected to the control module and the change in capacitance is interpreted by the microprocessor to mean that the user has placed the unit in position for medication ad minis- tration.

In alternate embodiment, the bottom end sensor 806 could initiate an administration cycle by first actuating an iris micromotor (not shown) to open the iris 320, and a sensor or limit switch or the like that is triggered when the opening 12O is fully exposed to indicate that the control module should terminate the actuating signal. The control module can send a closing actuating signal to the micromotor 806 to re-cover the opening 12O when the injection cycle is complete. Otherwise, the user will manually re-close the iris 320. The USB port 26 enables communications between the unit and associated peripheral devices (not shown), as well as permitting uploading of information to the ROM and downloading information therefrom. The control module is configured to permit recharging the battery via a power cord, attached to the USB port.

In accordance with the discussion above, the communications module 700 can provide one or more modalities for communications with systems external to the unit 10. Wi-Fi circuitry 770 under the control of the control module can enable communications with remote locations via a broadband wireless connection to the Internet if the unit 10 is sufficiently close to a Wi-Fi router. This enables information to be sent and received by the unit wirelessly at very high speeds. Another possible communication modality is provided by cellular telephone circuitry 772 for dialing remote locations under the control of the control module 500. The cellular telephone circuitry can be so-called 3G or 4G circuitry for connection to the Internet when connection to a WiFi router connection cannot be made. The unit 10 can further include GPS (Global Positioning System) circuitry 774 that transmits signals to a GPS satellite to indicate the global longitude and latitude of the unit. Finally, the unit can include Bluetooth circuitry 776 for wireless connection to a peripheral device such as a user's cellular telephone or personal digital assistant (not shown) that itself has Wi-Fi, cellular telephony, and/or GPS capability. These components can perform all of the functions and achieve all of the purposes described in U.S. Pat. No. 8,206,340, which are incorporated by reference herein, as well as those discussed herein further below.

The LCD display 18, the touch device 20, the speaker 22 (and headset, if provided), the microphone 24, and the cameras 25F and 25R are all discussed above in connection with FIGS. 1 to 3. These components comprise elements of a user interface UI by which information can be passed between the user and the unit 20. For example, the microprocessor can incorporate speech recognition software that enables the user to use spoken commands to operate the unit 10 via the microphone 24. In a more preferred embodiment, the microprocessor can incorporate elements of artificial intelligence to facilitate understanding of user commands and responses thereto on the display 18 and over the speaker 22. That is, with this feature, the commands do not have to be in a preordained format or use particular words to be understood by the unit microprocessor. It is anticipated that more useful embodiments of the unit 10 will be developed as the capabilities of artificial intelligence and speech recognition increase over time. An optional vibration device VM is shown in FIG. 13 to indicate its functional relationship to the other components of the unit 10, and some of its uses are described in a moment in connection with the use of the unit. The vibration device will typically comprise a conventional a vibratory motor with a motor shaft that rotates a small eccentric mass at an angular velocity between 8,000 and 16,000 rpm, which is felt as a vibration at a frequency between about 130 to 270 Hz. Uses for the cameras 25F and 25R are discussed further below.

Initialization of the Unit

To perform the tasks described herein, the unit 10 requires initial set-up by inputting data from the patient's healthcare provider. In its most basic form, this involves loading data into die ROM in the device microprocessor that will enable the programs stored therein to calculate insulin dosages and specify treatment regimens based on the user-patient's tested glucose level. This data can be input using a portable USB drive (not shown) on which the necessary information has been stored by the healthcare provider and which is then plugged into the USR port 26, or by sending the information to the unit over the internet via a receiver included in the Wi-Fi circuitry 770 or the cellular telephone circuitry 772 included in the unit. In addition, the programs stored in the ROM can be loaded, updated and/or changed in similar manners.

The necessary data is loaded into the unit's ROM by the healthcare provider so that it is available when the patient uses the unit. The data would typically include information such as insulin dosages and types and amounts of glucose-producing substances to be consumed based on tested blood glucose levels, and any other data or parameters required by the algorithms in the ROM used by the unit to determine a given insulin dosage or amount and type of glucose-producing substance to be ingested appropriate to a patient's tested blood glucose level. The exact nature of this data does not form a part of the present invention, and literature such as the references discussed in U.S. Pat. No. 8,206,340 illustrate the type of data and programs that can be used in this regard. Further details regarding exemplary patient data that can be loaded into the unit ROM to enable it to perform its intended functions can be found in the '340 patent, and are specifically incorporated herein by reference.

Performing a Treatment Cycle

Figure 14A:
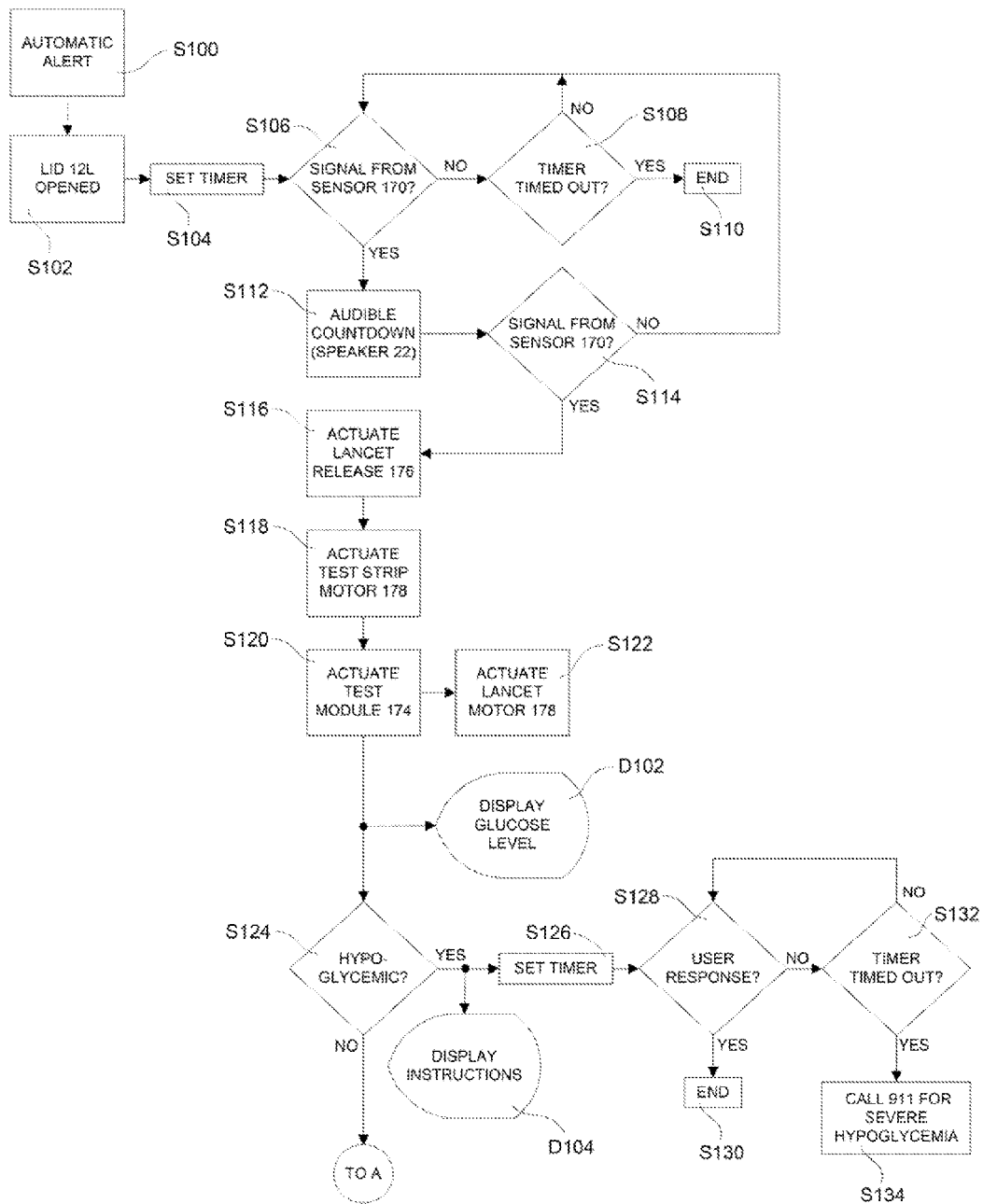
FIGS. 14A and 14B, is a flow chart illustrating a testing cycle directed by the unit in accordance with one embodiment of the invention.
Figure 14B:
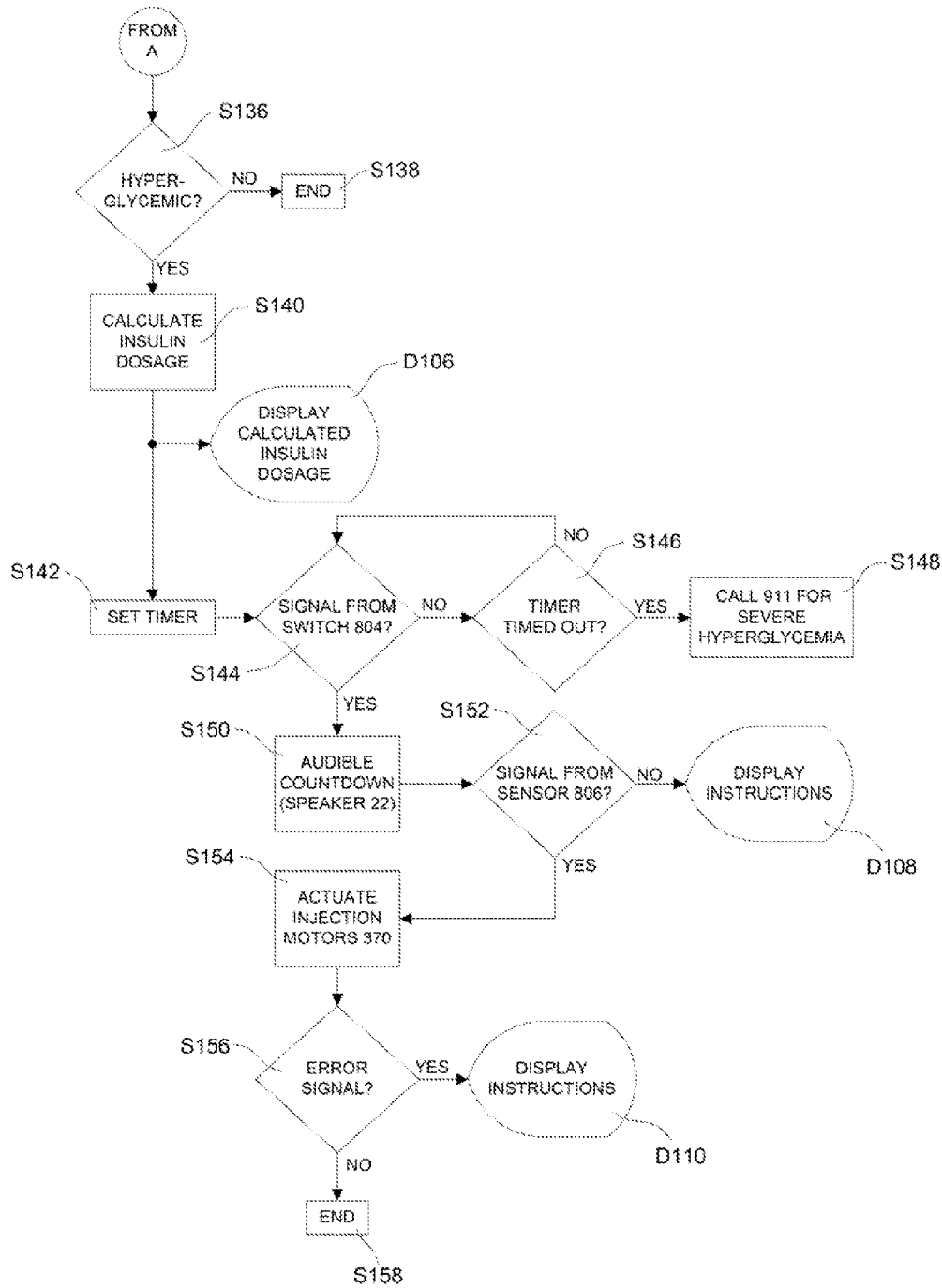

FIG. 14 (comprising FIGS. 14A and 14B) is a flowchart illustrating salient points in a test cycle comprising sampling a user's blood glucose and administering glucose or insulin, as directed by the unit 10 as thus far described. It will be understood as the following description proceeds that not, all functionalities of the unit are represented by entries in the flowchart. Rather, FIG. 14 is intended to show how the unit 10 described herein effects a glucose testing/insulin administration cycle. The unit 10 described herein can also effect some or all of the functionalities illustrated in the flowchart in FIGS. 6A, 6B, and 6C of U.S. Pat. No. 8,206,340 and described in the text accompanying that flowchart. Those portions of the '340 patent are specifically incorporated herein by reference, and those skilled in the art will understand from the following description how such functionalities described in the '340 patent can be incorporated into the testing cycle described in connection with FIG. 14 hereof. It is assumed here that the unit is in its ready condition, with the lid 12L and the iris closure 320 in their closed positions, and the lancet 122 in its armed condition.

A test cycle can be initiated in various ways. In the example illustrated in FIG. 14, the unit ROM stores information regarding scheduled glucose testing for the user, and generates a prompt to the user at step S100. This prompt can take one or several forms, including one or more of actuating the vibration device VM, displaying a prompt on the LCD display 18, and/or providing a verbal prompt using the speaker ("It is time for a glucose test"). In step S102 the user opens the lid 12L on the device by rotating it to expose the testing window 12W. This triggers the lid switch 802, which causes the microprocessor to start a timer in step S104. The process line between steps 100 and 102 is dotted to indicate that the user can initiate a test cycle manually by opening the lid 12L in the absence of a prompt from the unit (step S100). The unit can be programmed to audibly prompt the user to place his or her finger over the window 12W in position for piercing by the lancet ("Place your finger on the tester"), and/or display the same or similar prompt on the LCD display 18. In step S106 the unit waits for a signal from the finger sensor 170 indicating that the user has placed his or her finger over the window 12W. The unit can also display any of the same prompts, messages, and/or signals discussed in connection with the display box D102 in FIG. 6A of the '340 patent. The timer is typically set for between 10 seconds to one minute, and more preferably for 30 seconds. If the timer times out in step S108 before the ROM receives a signal from the finger sensor 170, and the test cycle was initiated by a prompt from the microprocessor (step S100), the unit will record this fact and can, under certain circumstances (say, if several prompts have been ignored) notify the user's healthcare provider or an emergency service provider such as the public 911 system or a private system such as the Alert One® medical alert service provided by Alert One Services, Inc., of Williamsport, Pa.

If the finger sensor 170 does sense the presence of the user's finger at the top first end of the unit before the timer times out, the process proceeds to step S112, in which the unit begins an audible countdown over the speaker of the time by the second ("5, 4, 3, 2, 1") until release of the lancet 122, with an optional display of the countdown on the LCD display 18. At the end of the countdown, the ROM checks at step S114 to see if there is still a finger on the window 12L. If not, the process returns to step S106, and in the absence of a signal from the sensor 170, the unit proceeds through the time out step S108. If the timer has by now timed out, the process proceeds to step S110, which ends the process as discussed above. If the sensor 170 detects the presence of a finger on the window 12W, the process proceeds to step S112 as before and a new countdown starts.

If the signal from the sensor 170 is present at the end of the countdown (step S114), the microprocessor actuates the lancet release solenoid 174 in step S116 to draw blood from the user's finger and onto the test strip 112. After a brief pause, the test strip motor 172 is actuated in step S118 and the test strip with the blood sample is moved into the housing 110 where the test module 174 determines the blood, glucose level in step S120. Thereafter, the lancet motor 178 is actuated in step S122 to retract the lancet 122 and re-latch it in its armed condition, as described above. At the same time display status box D102 displays the blood glucose level on the display 18 as shown in FIG. 8. It will be appreciated that the unit can also announce the blood glucose level over the speaker 22 (or headset), which is a particularly useful feature for visually impaired users. If the user is hypoglycemic as determined in step S124, the process will display instructions to the user at display status box D104 and set a timer in step S126. The timer waits for an appropriate response from the user in step S128, and if the user responds the process terminates at step S130. If the user does not respond before the timer times out in step S132, the unit takes appropriate action, which can be an automatic call to 911 in step S134 if the user's blood glucose level is so low that the user might be in danger. It will be appreciated here that the unit 10 can perform all of the steps in the process described in the '340 patent if the blood test reveals a hypoglycemic condition. For example, the unit 10 can store the threshold levels L1 and L2 as shown in FIG. 6 of the '340 patent, and the process performed by the unit 10 herein can include some or all of the steps described in '340 patent when the user tests hypoglycemic.

If the user is not hypoglycemic, the process proceeds to step S136, where the tested glucose level is compared to the user's hyperglycemic threshold as stored in the unit's ROM. If the user is not hyperglycemic the process ends at step S138. If the user is hyperglycemic, the protocol followed by the unit 10 is comparable to that described in the '340 patent and illustrated in FIG. 6 thereof. For example, as was the case if the user tested hypoglycemic, the unit herein can also perform all of the corresponding functions described in the '340 patent if the blood test determines that the user is hyperglycemic. This would include storing threshold levels L3 and L4 as described in the '340 patent and performing some or all of warning, displaying, and prompting steps described there when the user tests hyperglycemic. The description of those steps is truncated here for the sake of simplicity and to highlight the functions of the present unit that are not explicitly disclosed in the '340 patent.

If the user is hyperglycemic, the unit calculates the insulin dosage in step S140, and displays the results in display status box D106, preferably in the same general fashion as in the '340 patent (see FIG. 7 and column 15), and sets a timer in step S142. The display can then request that the user confirm the calculated dosage amount (using the input device 20 or by a speech command such as "OK"). As in the device described in the '340 patent, the user can also set a different dosage. The unit then prompts the user to turn the actuating ring 330 to expose the opening 120 for the needle 302. This can be done audibly ("Please prepare for insulin injection"), by a message or graphic on the LCD display 18, or both, indicating the action required. The timer is typically set in step S142 for a first predetermined time of between 10 seconds to one minute, and more preferably for 30 seconds. The amount of time should be sufficient to enable the user to perform the necessary action. In an alternate embodiment, the unit includes a motor that automatically opens the iris 320 and informs the user when it is ready for the insulin injection.

Once the timer is set, the microprocessor waits in step S144 for a start signal from the ring switch 804 indicating that the iris closure 320 has been opened to expose the opening 120 for the hypodermic needle. If the timer times out in step S146 before the iris closure has been opened, the unit takes appropriate action, such as calling 911 in step S148 in cases of severe hyperglycemia. As already noted, in the case of a user that has tested hyperglycemic, the unit can take any of the actions or operate in a fashion that incorporates some or all of the features of the device discussed in the '340 patent and the flowchart in FIG. 6 thereof. If the microprocessor receives a start signal from the ring switch 804 before the timer times out, it prompts to the user to place the unit at the intended injection site. This can be done audibly using the speaker 22 ("Please place the unit end on the injection site"), or by a message or a graphic on the LCD display, or both. In step S150 the unit begins an audible countdown by the second ("5, 4, 3, 2, 1") over the speaker of a second predetermined time until injection, with an optional display of the countdown on the LCD display 18. At the end of the countdown, the ROM checks at step S152 for a sensing signal from the bottom contact sensor 806 to determine if the unit is in place for the insulin injection. If not, the process takes appropriate action. This can take the form of repeating instructions to the user or requesting some other user response, which can be made audibly in a louder or more insistent tone. The unit can accompany these audible warnings by displaying a warning on the LCD display as indicated in display status box D108. The display can be made on a flashing red background on the display 18. The unit can also provide an audible alarm over the speaker 22, accompanied by a spoken message that a call will be made to an emergency service provider if the alarm is not disarmed within a predetermined time (typically no more than 45 seconds). The user can disarm the alarm and re-start the injection process at step S150, by providing a predetermined input to the unit using the touch device 20 or speaking a predetermined phrase into the speaker, or both. The predetermined input and/or phrase are designed to ensure that the user has not become disoriented or lost consciousness. Instructions for restarting the injection process can be shown on the display, as indicated in display status box D108.

If a signal from the contact sensor 806 is present at the end of the countdown in step S150, the process proceeds to step S154, where the Injection motors 370 are actuated to administer the microprocessor-calculated or user-set insulin dosage, as the case may be. Step S156 indicates that the error sensor 372 monitors the progress of the injection and if it detects an error or malfunction, it terminates the injection, displays a message ("An error has occurred during injection") and instructions to the user ("please contact your healthcare provider immediately"). In a preferred embodiment, the unit, automatically sends a notice of the malfunction and its nature using the unit's the communications module 700 to the unit manufacturer and the user's primary healthcare provider. This can be done wirelessly, and can include information on the location of the user. It can advantageously be provided via cloud-based ecosystems, such as the Smart Rep™ system discussed further below. In fact, such malfunctions exemplify advantages of integration of the unit into an ecosystem with components like the Smart Rep™ system, to allow automatic replacement of defective units, compilation of a database of malfunctions and their nature for manufactures and regulatory agencies.

If the Injection is completed successfully, the sampling/administration cycle terminates at step S158. At this time, the unit can audibly inform the user that the injection was successful and confirm the dosage administered. It can also state, and display on the LCD display, a message informing the user of the next scheduled blood sampling scheduled in accordance with the treatment protocol stored in the unit's ROM. The termination procedure will preferably include notification to one or more of the remote systems discussed below (such as the Smart Rep™ system and/or the Global EMR™ system discussed below) of a successful treatment cycle and particulars thereof, such as the date and time of administration, whether the user was hypo- or hyperglycemic, the amount of insulin injected, if any, and whether the amount of insulin injected was calculated by the microprocessor or set by the patient, just to name a few examples.

Variations, Modifications, and Enhancements

Those skilled in the art will recognize that many variations and modifications of the disclosed embodiments would fail within the scope of the invention, in one variation on the techniques described above, the testing/treatment history of a user can be downloaded via a bar code displayed on the LCD display 18 rather than by using an external USB drive or an Internet connection. In this variation, the unit's software can include an algorithm that converts recorded data into a bar code format that is then displayed on the LCD display. Scanning the bar code transfers the information to the scanning device. If necessary, the information can be contained in multiple bar code displays, which are then scanned in turn.

In another variation, the unit can include a removable USB storage device on which the data is recorded. This will facilitate manipulation and transportation of the recorded information. For example, such a storage device could be employed to eliminate an intermediate step in which the unit must be connected to a computer through a US port, as discussed. It will also enable a user to mail or otherwise transport the recorded data to a healthcare provider, for those users not comfortable with transmitting data over the Internet, as well as eliminating the need to visit the healthcare provider simply to have the recorded data downloaded onto a computer at the provider's location. If a removable USB storage device is used, the unit can be provided with multiple such devices so that the user has a supply on hand.

In emergency situations, the unit's location sensing circuitry (for example, via GPS or a cellular network) can locate the closest medical facilities such as a hospital, ambulatory center, clinic or standalone emergency rooms. It can also permit communication directly with such facilities to find the one that is best equipped for the ongoing emergency. The unit's alerting function can further be programmed to notify nearby relatives or caregivers (within, say, a predetermined distance from the user's location) of an ongoing emergency situation and the medical facility where the user is going.

In one enhancement, configuring the unit with a two-way communication platform such as Apple-like Face Time, Skype™, or any other like communication service that permits using the camera 25 for remote consultations with healthcare providers. These consultations can be provided as part of a general healthcare routine, or in connection with a current situation for which the user needs specialized guidance analogous to the subscription OnStar® service provided to automobile drivers). In that connection, the same service can function as an emergency service provider as discussed above, in which someone at the service provider can provide real-time advice during an emergency. Of course, this enhancement can be provided without a video link (that is by audio only), as well. Cameras on the front and the rear of the unit provide flexibility of use to patients and healthcare providers who might from time to time be users of the unit. (It should be understood that throughout this description, the term "user" is not restricted to a patient using the unit for monitoring, administration, or communication purposes, and references to a "user" will be clear from the context in which the term is used herein.)

In still another variation, medications can be administered by any means that serves the purpose of delivering them to the user in any appropriate manner. For example, instead of a hypodermic needle, a medication can be administered with a jet injector syringe that uses a high-pressure narrow jet of the injection liquid instead of a hypodermic needle to penetrate the epidermis. This type of device is powered by compressed air or gas, either by a pressure hose from a large cylinder, or from a built-in gas cartridge or small cylinder.

In yet another variation, the administration module of the unit described above can be adapted to administer two or more medications. Many individuals have co-morbid diseases for which they are being treated and for which they are prescribed multiple medications. It is not unusual for a person to be taking four or more different medications, usually on a different schedule for each. This can cause confusion leading to medication errors, which can cause avoidable side effects and negative outcomes. A unit according to this variation could take many forms. For example, the administration module could include a revolving chamber for dispensing different medications, or incorporate interchangeable administration modules for different treatments. The unit could be programmed to provide instructional prompts (audible, text, video, or any combination) tailored to an individual's particular treatment protocol. In that regard, individual administration modules can have electronic identifying indicia that the unit can read and match with prestored instructions to provide instructional prompts appropriate to particular medications. All activity of the user related to a given administration module is stored for upload to a healthcare provider of an ecosystem (as described below) for the purposes discussed below.

The following are a few examples of multi-medication treatment regimens possible with this type of unit:
HIV cocktail therapy:
    HAART (Highly Active Anti Retro Viral therapy) cocktail (administered orally or by injection, for example)
    Multi drug resistance combinations (administered orally or by injection, for example)
    Treatment for HIV or AIDS opportunistic conditions such as sarcomas, pneumonia, influenza, tuberculosis, hepatitis, etc. (administered orally, by injection, in ointment form, intravenously, to name some examples)
Vitamin assortment of vitamins for wellness programs (administered orally or by injection, for example)
Multiple medications to manage diabetes:
    Metformin tablets
    Sulfonylureas-treatment of type-2 diabetes (administered orally)
    GLP1 (administered orally or by injection, for example)
    Insulin injections.

Another variation of the unit described above is adapted for use independent of a sampling module, and may be constructed without a sampling module at all. This type of "smart injector" could alternatively be constructed with a switch or other means (voice activated, for example) to disable the sampling module 100. It could also permit a user to install different administration modules with electronic identification indicia to enable a user to interface with the administration module using a suitable input device like the touch device 20 and/or display, or by voice activation using voice recognition software as discussed above. In one mode of operation, the user can set a dosage amount to substitute for step S140 in the flowchart in FIG. 146, after which an exemplary process would proceed by incorporating some or all of the subsequent steps described above in connection with FIG. 14B. Of course, such a unit could be used for medications other than insulin in accordance with the discussion further below of other applications of the unit 10.

Further, a comparable unit could be adapted for use without an administration module, or constructed without an administration module at all. Such a unit could perform some or all of the steps described in FIG. 14A, tailored to a specific medical condition (that is, conditions other than diabetes; see discussion below of other applications of the unit). Such a unit would provide a way of monitoring medical conditions that are not necessarily life threatening, but as to which it would be advantageous to permit a patient to periodically check some bodily condition using a portable unit, and communicate the results to the patient's healthcare provider. It would also provide a way of keeping an individual's healthcare provider apprised of the status of his or her medical condition, without requiring an office visit. And it would provide all of the data recording and utilization features described in the next section.

Data Recording/Utilization—Integration with Companion Systems

Another aspect of the invention involves storage in the microprocessor's ROM of complete information regarding the timing and results of the blood glucose testing, times and amounts of ingestion of blood glucose producing substances, times and amounts of insulin injections, calls to 911 and/or a private subscriber service, or any other aspect of the process just described. Many of the instances where recording is performed are noted specifically in the above description, and others will be apparent to those skilled in the art. The recording capabilities of the unit enable compilation of a complete history of a patient's monitoring and management of his or her condition that various entitles can access for numerous uses. As described more fully in U.S. Pat. No. 8,206,340, one such entity is the patient's healthcare provider, which can download stored information and employ it for various reasons, such as making adjustments to the patient's treatment protocol, which can then, be uploaded to the unit as discussed above. The same information, collected from numerous patients, can be used for public health purposes by converting it to statistical information on treatment of diabetes or other conditions as described further below. All of the uses described in U.S. Pat. No. 8,206,340 for data stored by the unit described there are also available in connection with the unit 10 described here.

The recording and storage of information concerning the use of the unit for the purpose of monitoring and managing a single patient's medical condition also enables the unit to be integrated as part of an entire healthcare "ecosystem." Such an ecosystem could have a multitude of functionalities and embodies concepts that are independent, of the medical condition the unit is used to monitor and treat (Specific applications of the unit, for other than diabetes monitoring and treatment are discussed in the following section). This ecosystem can have numerous parts that interact with a unit according to the present invention and with each other to realize multiple advantages, including enhancing patient outcomes, improving public health data gathering, providing information required by regulatory agencies, and facilitating the exchange of information with insurance carriers, just to name a few.

Parts of such an ecosystem have already been described above in connection with the usage of the unit 10 and in the '340 patent. These include the notification of emergency service providers such as the public 911 system or private systems such as the Alert One® medical alert service. Another possible part of such an ecosystem could be specialized healthcare knowledge centers that offer medical advice to a patient-user of the device or his or her physician. Such advice would thus be adapted to specific aspects of the patient's condition as reflected by the monitoring and treatment history stored in the unit ROM and sent to the knowledge center by the unit's communication module. The knowledge center could download information to the unit regarding matters such as treatment protocols, recent developments in treatments for the patient's condition, and oral advice from a specialist physician to be recorded and played back by the user, just to name a few possibilities. The downloaded information, if in text form, can be automatically displayed on the unit's LCD display, or a prompt could be displayed indicating that a message (oral or text) is waiting. The healthcare knowledge centers can be existing organizations that specialize in certain medical conditions, such as Joslin Diabetes Center of Boston, Mass., or specialists at other organizations such as the Cleveland Clinic, Harvard Medical School, the Mayo Clinic, Johns Hopkins Hospital, or the like. Organizations such as these and others could offer their services to users of the unit, whether patients or physicians, either as a public service or on a subscription basis.

Figure 15:
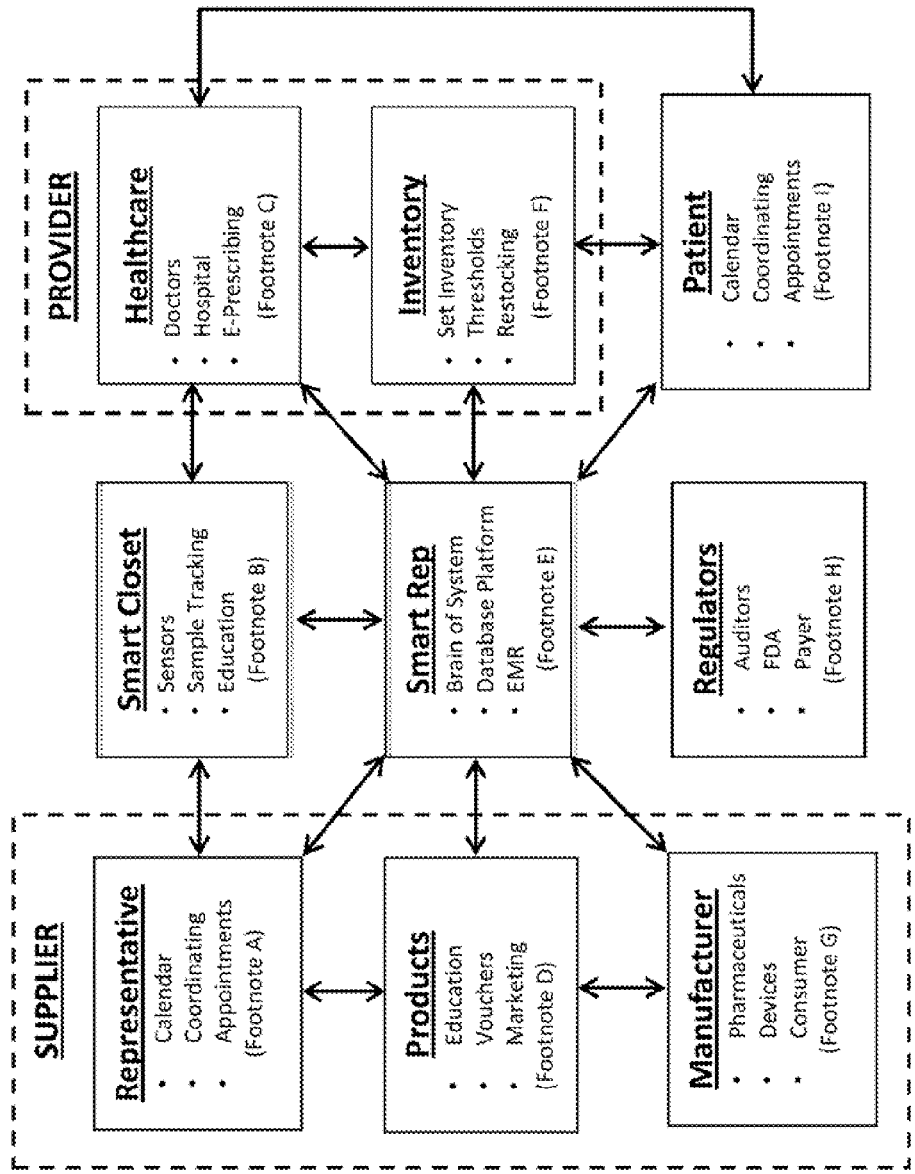
FIG. 15 is a diagram of an example of a cloud-based Smart Rep™ system of which the unit in FIG. 1 can form a part and which enhances the functionality of the unit in accordance with one of the aspects of the invention.

An ecosystem incorporating a unit as described herein could also comprise one or more components of a multi-purpose healthcare system such as that described in U.S. provisional patent application no, 61/705,961, entitled "Smart Rep System Healthcare Provider/Supplier Interface," which is incorporated, by reference into the present description as if set forth in full herein. FIG. 15 is a schematic diagram of various components of an exemplary Smart Rep™ system that uses a cloud-based server to track, monitor, store, and report interactions among numerous parties to coordinate myriad activities relating to individual medical care of individuals participating in the system via the unit 10 with the capabilities already discusses and to public health. The footnotes referenced in FIG. 15 explain the functions that the system components perform and how the components interact with each other:

(A) "Representative" comprises any pharmaceutical, device, and over the counter sales, marketing and medical representative from the manufactures identified in footnote G.

(B) "Smart Closet™" comprises the physical repository or storage area with sensors that monitor, record, and track the flow of items taken from or introduced to "inventory." This includes not only traditional health care items such as pharmaceuticals and medical devices, but also educational materials, inventory reports, marketing reports, etc., either printed or transmitted electronically from the Smart Closet™ repository.

(C) "Healthcare provider" includes doctors, dentists, nurses, and administrative personnel supporting care providers in all care centers, including hospitals, acute care centers, physician offices, hospices, pharmacies, etc. One feature of the system is that doctors can prescribe electronically (E-Prescribing), and patients (footnote I) can obtain prescriptions by accessing the server (footnote E). Patients can also physically receive items from a Provider.

(D) "Products" include all items identified in footnote G and all educational, sample voucher, and marketing materials.

(E) "Smart Rep™" is the preferably cloud-based server system that tracks, monitors, stores, and reports interactions between the parties in FIG. 15. Access is typically available to subscribers (and patients of subscribers), and regulatory agencies. Available information and/or services can include data interchanges incorporated into electronic medical record (EMR) systems. If the unit 10 is integrated with this type of system, a user would typically connect to the Smart Rep™ system server represented here, preferably using one or more of its wireless communication devices.

(F) "Inventory" includes all Smart Closet™ information and product movement and stocking information for the use and replenishment of supplies.

(G) "Manufacturer" includes any producer of branded or generic pharmaceutical products and devices, as well as a provider of services to the healthcare industry. It can also include manufacturers and sellers of consumer products, such as over-the-counter, non-prescription medications, wound care products, and other consumer healthcare products.

(H) "Regulators" comprise federal, state, and national regulatory and auditing agencies involved in monitoring the healthcare industry. It can also include a payer of healthcare expenses, such as a private insurance company, Medicare, Medicaid, etc. These parties can use the system for purposes such as detecting fraudulent activity, identity theft, or other kinds of misrepresentation.

(I) "Patient" is the actual patient or his/her family members and/or caregiver. It can also include other care providers and/or organizations requiring access to information about the patient's medical care. Patients have access to the Smart Rep™ server to schedule appointments, obtain test results, access medical information, etc. It will be appreciated that the term "patient" is used broadly in this context, and will include any user of a unit with some or all of the capabilities of a unit as described herein. It will also be clear that it is contemplated that myriad users will be part of a Smart. Rep™ system as described herein.

For example, the unit described herein can communicate with the server of the Smart Rep™ system to upload stored information regarding any aspect of the testing and medication administration protocol performed by the unit (whether relating to diabetes care or other applications discussed further below). For example, the unit 10 could communicate to the server that the testing cartridge or the injection cartridge is empty and needs to be replaced. The Smart Rep™ system can automatically arrange to send to the user replacement cartridges, new test strips (which may be separately replaceable in certain embodiments), or any other consumable part of the sampling module or administration module item. The system can further keep track of the central inventory of such items (via the Smart Closet™ inventory control feature of the Smart Rep™ system) to ensure that an adequate supply of replacement cartridges and other consumable items is always on hand. Information on the testing and medication administration history of numerous patients can be collected by other Smart Rep™ system participants for use by public health agencies, healthcare providers, medical supply distributors and manufactures, regulatory agencies, and insurance companies, to name just some of the possibilities.

It will be appreciated that a supporting infrastructure like the Smart Rep™ system can be provided with almost countless ways of assisting the user in managing a medical condition. Examples include the ability to write or refill prescriptions and communicate them to the unit or a pharmacy or both. For example, information recorded and sent to the Smart Rep™ system by the unit can be analyzed by a healthcare professional participating in the system, who might determine that a patient's medication should be changed, or that the patient's condition requires treatment other than medication administered by the unit. In such a case, a prescription for the new medication could be sent, directly to a pharmacy that the patient has previously designated to the Smart Rep™ system (possibly by using the unit). An optional feature would send a prompt for display on the unit or a voice message to indicate that a prescription has been sent to the user's pharmacy.

It will be recognized by those skilled in the art that the ecosystem could also include a separate cloud-based system for supplying replacements of consumable components of the unit described herein. That is, the ecosystem incorporating the unit, can include a resupply system rather than or in addition to relying on a similar capability in the Smart Rep™ system for consumables, such as the administration module, the sampling module, the alcohol tablet batteries, and any other item in a particular unit that needs to be periodically replaced. Depending on the capabilities and the application for which the unit is adapted (see further below), this resupply aspect of the system could monitor usage and/or performance of various components of a unit and arrange for automatic ordering of replacements (or for prompting the user that replacements are necessary) for items such as (a) oral medications, inhalers, nasal sprays, nebulizers or other mist-related medication devices, drops and other types of inner ear medications, dermal or intradermal treatments, ointments, vaccines, elixirs, and powders, whether administered by the unit or are used in connection with the condition monitored using the unit, (b) other consumables, such as lancets, testing strips, assays, dyes, and reagents, that are used in connection with the sampling and testing function of a unit and that are depleted as the unit is used over time, and (c) hardware components such as computer memory, application chip sets, telecommunication devices, and the like that can fail and require replacement. Supplies could further be color coded, bar coded, and/or be provided with an RF tag or the like, for identification by a reader/detection device that cooperates with software in the unit and can read or detect the identification information to verify that the item is intended for that particular user. The unit could be programmed to display information about the item to enable further confirmation by the user that it is intended for his or her use.

Another part of such an ecosystem can be the IMOS™ platform and operating system, which provides integrated medical information system software and services that in one aspect enable communications between a unit as described herein and one or more peripheral ancillary devices such as an electronic sphygmomanometer, weight scale, spirometer, electrocardiogram, stethoscope, digital signals representing the results of diagnostic tests such as ultrasound, Xray, CAT, and MRI examinations (or from any other diagnostic testing technique), pupillometer, calorimeter, dosimeter, thermometer, or any other device that provides information in digital form indicative of some condition of a person or animal. These and other types of ancillary devices can communicate with the unit either by a wired connection, such as via the USB port, or wirelessly to periodically or continuously monitor a patient's condition, and in the typical case would take the place of the sampling module. The IMOS™ operating system provides the platform for sharing the results of such tests with the unit in a form that the unit can utilize for all of the purposes described herein. The unit can also store this information in its ROM and upload it to a healthcare provider or healthcare knowledge center of the type discussed above participating in the IMOS™ platform, and then be used to provide treatment instructions or other information to the patient via a download to the unit for display or voice communication over the unit's speaker. The IMOS™ platform can also be integrated with systems and organizations that collect information capable of providing information and support in connection with the use of units like those described herein. These can include organizations that collect information for medical and healthcare purposes such as universities, research labs, information service companies, philanthropies, insurance carriers, regulatory agencies, and the like.

The supporting ecosystem of which the unit is a part can also include a universal health record system that integrates all aspects of the user's current and past treatment history for use by healthcare providers granted access by the user. This Global EMR™ electronic medical record system would be a cloud-based service that could store the entire medical and dental records of an individual (whether human or animal), including information recorded, stored, and uploaded to a server by a unit as described herein and by other components of the ecosystem already described. The user would control access to the records with a secure password and authentication scheme and the entire system would use firewalls in a known manner to comply with governmental regulations concerning privacy.

Some or all of these parts of the ecosystem can make uses of data that a unit as described herein can record and store, or that can be collated using information provided from plural such units:

Assemble statistics (global, national, regional or local) relating to healthcare issues such as correlations between diagnoses and prescribed treatments, costs of particular services provided to users and benefits realized from them, correlations between treatments and outcomes, correlations between life expectancies and the prevalence of particular diseases and cures, and between the provision of healthcare samples and outcomes (for example, determining the correlation, if any, on a person-to-person basis between samples of medications given to individuals in certain demographics— for example native Americans—and control of blood glucose levels)

identify subgroup populations benefiting from a particular clinical trial or drug Gather data regarding exclusion patient populations due to reported adverse events as associated with and correlated to bodily fluids, DNA/RNA biomarkers, enzyme, etc., such as patients with biomarkers, blood types genes, etc., that exclude them from taking certain medications.

Allow commercial entities such as pharmaceutical companies or vendors participating in the ecosystem to do many tasks based on data heretofore difficult to collect, such as:

Devise mass marketing approaches that target marketing information and education programs for patients with certain medical conditions and required treatment protocols Organize global distribution and branding platforms to provide logistical and sales support, based on the prevalence of certain kinds of diseases in various geographical areas or among certain demographic groups Correlate the volume of sales or prescriptions for a particular product with the number of promotional samples that were given away Determine how many of a vendor's customers have reordered products as they are consumed by users of the unit, including determining numbers of products per order Compile users' satisfaction ratings of physicians, diagnostic devices, products, or services Compile and collate into categories types of questions or concerns users have communicated to healthcare providers or other suppliers.

The IMOS™ operating system platform for the unit and the ecosystem components facilitates the communications and operations discussed above. For example, it enables participants in the Smart Rep™ system to sync information on all parts of the system, while providing controlling or restricting access to certain information, either designated confidential or protected by government regulations. Syncing information across the various components of a system such as the Smart Rep™ system will enable calendars of various participants to be synchronized to facilitate tasks such as meeting planning and patient visits to various healthcare providers. Another example of the functionality provided by the IMOS™ operating system platform would be to enable various participants in the Smart Rep™ system and in the Global EMR™ medical record system to share medical records of a patient that includes data and information provided via the units as described herein being used by multiple users.

The ecosystem can also include Healthmart™, a cloud-based supplier of programs designed to help the user perform specific tasks ("apps") related to healthcare issues of interest or importance to the user. These apps could include programs downloaded to the unit from a Healthmart™ app supplier. The following are examples of tasks that such apps could perform;

- Direct users to information on health care, nutritional supplements, wellness, price comparisons of healthcare products and services, and/or other health or veterinary related subject matter
- Provide an avenue for users to suggest directly to providers such as the unit manufacturer, pharmaceutical companies, or any other participant, in the Smart Rep™ system ideas for new products or product improvements or additional, services or improvements in existing services
- Provide either via the Healthmart™ app or a separate HealthRank™ app a mechanism for users to grade service providers (such as physicians and hospitals); users' rankings could be uploaded to the Smart Rep™ system for access by participating insurance companies, government agencies, etc., or shared among users
- Enable direct audio or video communication between a physician and patient, or access to physician narrated instruction/informational videos using DOKTOK™ two-way communication software
- Provide an avenue by which a user can report directly to providers such as the unit manufacturer, pharmaceutical companies, or healthcare providers adverse events or side effects such as fainting, dizziness, rashes, nausea, headaches, pain, or other difficulties
- Provide an avenue for a user to submit questions to the customer service department, of products or services used with a unit
- Permit a user to download coupon vouchers or special offers on consumer healthcare products or over the counter medications
- Provide direct interunit communications so users of units can communicate with each other directly (either in person, by e-mail, via social media, text, messages, or otherwise) in groups or on a one-to-one basis.

A further feature of the ecosystem can include notification of severe patient adverse events to ecosystem participants, such as one or more of a patient's healthcare providers and emergency medical first responders. In addition, family members and/or caregivers can be notified each time the unit provides an emergency notification. As already discussed, the unit can use its GPS circuitry or position information gathered by other means to determine the user's location and upload this information periodically to the ecosystem, so that a failure to update at the appointed time can be detected by appropriate software in the ecosystem server to fix the last known location of dementia patients or children if a predetermined number of updates are missed. In general, the types of synchronized communication among various participants in the ecosystem can avoid errors and omissions, and resultant poor patient outcomes, that have plagued healthcare rendered using known technology.

Applications for the Unit

In the description of the constructional details and operation of the unit 10, diabetes management and treatment was used as an exemplary application. However, there are many other applications for such a unit, and there are many systems with which it can coordinate and communicate. The unit, can be adapted for sampling and testing a wide variety of bodily fluids depending on the condition to be treated/monitored. Examples of such bodily fluids in addition to blood include sweat, urine, and saliva. It will also be appreciated that the unit can test for many properties other than blood glucose level and administer treatments based on the test results. Broadly speaking, the invention includes measuring and/or analyzing all types of assays across multiple analytes and sample types, including tissue samples, breath samples, light, sensors, and the like for use in testing based on properties of one or more of DNA/RNA, proteins, enzymes, biomarkers, gene mutations, gene sequencing, oxygen levels, $CO_2$ levels, or any other measurable substance or genetic indicator in a living organism. It can also integrate information from other sources, such as the ancillary devices discussed above, to take samples and determine appropriate treatment regimens. In that regard, it will be appreciated that the unit can be in the form of a mobile device as described herein that administers medications using a delivery system that can take any suitable form such as an administration mechanism of the type already described, it can also include combinations of medication delivery mechanisms, such as one or more of an administration mechanism like that described further above, an inhaler, an oral dispenser, a liquid dispenser, a nasal spray, a nebulizer, a mist generator, a respimat soft mist inhaler, and others.

Given that broad range of sampling/testing/treatment possibilities, it will be apparent to those skilled in the art that there are myriad applications for treatment of a wide variety of medical conditions using a unit in accordance with one of its core concepts of the invention, namely a unit that includes in combination: (i) a mechanism for taking from a patient a sample, which is defined for present purposes as measuring a bodily condition of the patient, (ii) circuitry such as a microprocessor for determining a treatment based on a test for a particular property of the sample, and (iii) a mechanism for administering a treatment based at least in the first instance on the determination by the circuitry (although in another aspect of the unit a user could override the recommended treatment). The following are some exemplary applications other than diabetes control for a unit in accordance with the present invention.

Opiate Overdoses and Pain Medication Misuse

This application involves using a protocol that includes injecting nalaxone opioid inverse agonist to counter the effects of an overdose of an opiate such as heroin, or morphine. A key indicator of such a condition is respiratory depression, which can be measured using a unit in accordance with the invention constructed with a sampling mechanism incorporating an oximeter for measuring blood oxygen levels. Another indicator of an opiod overdose is a change in normal chest wall movement, which can be measured by incorporating an accelerometer into the unit in addition to or instead of an oximeter. The unit would already have stored therein the patient's baseline blood oxygen level and chest movement data.

Using the results of tests based on samples taken by the oximeter or accelerometer, the unit microprocessor can calculate an appropriate dosage of nalaxone in accordance with stored information relating to a stored profile of the user, including information such as the user's age, weight, allergies, etc. Nalaxone can be administered in three different modalities, intravenously, intramuscular injection, or as a nasal spray, and a unit is accordance with the present invention could incorporate an administration mechanism capable of nalaxone treatment using one or more of the three modalities, in emergency situations an emergency service provider (911) can be automatically notified of the user's condition and location (using the GPS or cellular telephone capabilities).

Pain Management

Pain from cancer (carcinoma) can be managed using a unit in accordance with the invention that samples blood $CO_2$ levels, which correlate to tachycardia and tachypnea, and/or changes in chest wall movement using an accelerometer as discussed above, all of which are indicators that a person is experiencing pain. Treatments would include opiates (such as morphine, with or without one or more adjuvants) and other types of analgesics such as non-steroidal anti-inflammatory medications.

A unit according to the invention would store the history of administrations of such medications, including information such as the time from the last administration, the frequency of administration, the amounts and types of medication administered in the past, the manner of administration, and the patient's responsiveness to previous administrations. These data could then be used by the unit's microprocessor to calculate a recommended dosage in accordance with established protocols based on a patient's age and weight.

The unit can include an administration mechanism that injects a dosage of pain medication in accordance with the calculated amount or an amount set by the patient manually by overriding the calculated recommended dosage. The ability of the unit to cooperate with an ecosystem as described in the examples given above that provides patient support would be an important component for this application. For example, a healthcare professional participating in the ecosystem could monitor patient information such as heart rate, respiratory rate, blood pressure, and $pCO_2$ to adjust treatment protocols and download them to the unit for use in calculating recommended amounts and frequencies of administration of analgesic medications.

Anticoagulant Therapy

This application involves the testing of blood clotting parameters such as prothrombin time (PT) and its derived measures of prothrombin ratio (PR) and international normalized ratio (INR), which are commonly used to measure the extrinsic pathway of blood coagulation. The sampling module of the unit can be adapted to measure this or other blood clotting parameters and calculate an appropriate dosage of an anticoagulant such as enoxapario (a low molecular weight heparin marketed under the trade names Lovenox®, Xapari, and Clexane®, among others). This medication prevents and treats conditions such as deep vein thrombosis or pulmonary embolism, and is administered as a subcutaneous injection.

Summary of Additional Applications for Unit

There are many other possible applications for a unit in accordance with the invention. Some others in addition to those already discussed in detail are described in tabular form in the following Table 1, which constitutes just a partial list of the types of conditions that can be monitored and treated using such a unit, with the nature of the sample, the substance or property tested, and the treatment administered for each.

TABLE 1

| Condition | Sample | Medication/Method of Administration | Comment |
|---|---|---|---|
| HIV | Blood or saliva | Stribild ™ (elvitegravir cobicistat emtricitabine tenofovir)/oral | Test determines presence of HIV antigen |
| Cholesterol | Blood | Lipitor ® (atorvastatin calcium)/oral | Test determines lipid panel or lipid profile; veterinary therapy may differ |
| Prostate cancer | Blood | Luteinizing hormone-releasing hormone agonists/subcutaneous injection, orally, cream/ointment, nasal spray, inhaler | Test for prostate specific antigen (PSA) |
| Allergies | Blood/skin test | Loratadine (e.g.)/oral, ointment, nasal spray, inhaler, injection | Medication depends on the allergy |
| Thyroid Disease | Blood/tissue/peroxidase (TPO) antibody test | Levothyroxine/oral or suspension | Suspension of crushed oral Levothyroxine used in pediatric treatment |
| Osteoporosis | Blood | Teriparatide (rDNA origin)/subcutaneous injection | Test for presence of one or more of rheumatoid factor, ESR, C-reactive protein, anti-CCP, ANA, HLAB27, anti-CPT, creatine phosphor kinase, and anti-DNA |
| Breast Cancer | Blood/biomarkers/biopsy/DNA-RNA, gene test | Traztuzumab/intravenous infusion, injection, oral | New technology enables detection of many cancers by indentifying biomarkers such as BRCA1 and HER2 |
| Kidney Disease | Blood/urine | Epoetin alfa/injection, intravenous | Microalbumin test |
| Liver Function | Blood | interferon and ribavirin/oral (tablets or liquid), injection | Liver function tests use groups of clinical biochemistry laboratory blood assays to provide information on liver condition |
| Hypertension | blood pressure | Rosuvastatin calcium/oral | Test with electronic sphygmomanometer (see note 1 below) |

TABLE 1-continued

| Condition | Sample | Medication/Method of Administration | Comment |
|---|---|---|---|
| Autoimmune diseases: Rheumatoid Arthritis Juvenile Arthritis Psoriatic Arthritis Ankylosing Spondylitis | Blood | Adalimunab/injection | Test for antinuclear antibody c-reactive protein (CRP), rheumatoid factor, and complete blood count CBC) |

Note 1:
The sphygmomanometer can be a peripheral device connected to the unit via the USB port; see further above.

It will be appreciated that the applications discussed in this section relate to known testing methods, medications, treatment protocols, and administration methods. The invention of course can be adapted to use tests, medications, protocols, medication administration methods developed in the future. For example, the invention contemplates including any later developed administration method involving technologies using nebulizer devices, misters, inhalers, ear drops, radiation, and intravenous administration, to name some possible examples.

Pediatric and Veterinary Uses

Pediatric care is generally defined as healthcare and medication for children generally under the age of 18 and include neonate, premature neonate, full term neonate, infant (one month to one year), child or children (1 to 12 years of age), adolescent (13 to 18 years of age), postnatal age, gestational age, and postmenstrual age. Pediatric care using the unit described herein has to consider the implications on smaller, younger people and bodies, taking into consideration growth, hormonal and other issues. To that end, the unit can be adapted to monitor, measure, and treat conditions for pediatric patients. This would include adjusting testing and measurement criteria, treatment protocols, communication methods, methods of administering medications, and methods of monitoring treatment. For example, on liquid injections, the amount of units administered and the needle size may vary for pediatric patients.

For veterinary purposes, the sampling, measuring, and administration functions will be similar in terms of operation, although different medications, dosing levels, and administration methods and frequency may be used in particular instances. The test portion of the unit's operation will of course measure different data points and use different algorithms to determine the appropriate treatment for the animal. For example, normal temperature and blood sugar level of a dog are different for different breeds and by age and weight for a particular breed. Accordingly, a unit for treatment of dogs could permit the human user to input the breed, age, and weight, and incorporate a ROM with algorithms that determine appropriate treatment protocols depending on that input. Similarly, the unit can be part of and supported by an ecosystem with features and aspects corresponding to those discussed above, but adapted to the veterinary application of the unit.

SUMMARY AND CONCLUSION

The above description relates to a universal testing/administration unit and system that can increase the probability of positive outcomes for patients with serious medical conditions. The unit and system in one broad aspect involve patient self-testing and/or self-administration of a treatment agent. The invention frees patients with such conditions to follow more normal lifestyles while enabling effective monitoring of their conditions and also providing for alerting healthcare and/or emergency providers if and when intervention may be necessary. The unit can integrate with wide coverage healthcare, business, and leadership networks, which in turn can interface with medical supply distributors and manufactures, public health agencies and regulatory bodies, among others, as part of "global" management of healthcare for a large portion of a given population.

Those skilled in the art will readily recognize that only selected preferred embodiments of the invention have been depicted and described, and it will be understood that, various changes and modifications can be made other than those specifically mentioned above without, departing from the spirit and scope of the invention, which is defined solely by the claims that follow.

What is claimed is:

1. A treatment administration unit comprising:
a housing of a size suitable for transport in a handbag or clothing pocket;
a sampling module in the housing operable to take a biological sample from a patient and test a property of the sample relating to a medical condition of the patient;
a microprocessor in the housing for operating the sampling module and determining the medical condition of the patient from the property tested by the sampling module;
an administration module in the housing including (i) a container for a substance effective to treat the medical condition and (ii) an administration device operable to administer the substance internally of the patient from the container under the control of the microprocessor, wherein a start signal is generated when operation of the administration device has been enabled;
a proximity sensor for generating a sensing signal when the unit is oriented relative to the patient for operation of the administration device;
a wireless communication device in the housing and under the control of the microprocessor; and
circuitry in the housing for detecting the location of the unit, wherein:
the microprocessor includes a treatment protocol memory for an individual patient that stores parameters for determining when the medical condition determined by the testing of the sample property presents a potential danger to the patient and a healthcare facility index with geographical locations and contact information for a plurality of healthcare facilities, the unit includes timer circuitry for measuring a time elapsed from the determination by the microprocessor that the medical condition presents a potential danger to the patient and for measuring a time elapsed from generation of the start signal, the microprocessor is operable to determine from the location of the unit and the healthcare facility index a location of a healthcare facility that can treat the patient, the microprocessor automatically operates the administration device to introduce the substance internally of the patient when the sensing signal is generated prior to the elapse of a first predetermined time after generation of the start signal, and the wireless communication device automatically notifies a healthcare facility of the existence of the medical condition presenting a potential danger to the patient and the location of the unit in the absence of a start signal before the elapse of a second predetermined time.

2. A treatment administration unit as in claim 1 further comprising a user interface in the housing, wherein the user interface includes a visual display and a speaker and is operable under the control of the microprocessor for receiving operational commands from a user of the unit and providing information to the user.

3. A treatment administration unit as in claim 2, wherein the user interface further includes at least one of a manual input device, a microphone, a vibratory device, and at least one video camera.

4. A treatment administration unit as in claim 3, wherein said microprocessor includes speech recognition software for converting voice signals received by the microphone into operational commands and artificial intelligence for facilitating understanding of user commands input via the user interface.

5. A treatment administration unit as in claim 1, wherein:
the sampling module includes an oximeter, the biological sample is the breath of the patient, and the property is the patient's blood oxygen level determined by the oximeter;
the medical condition presenting a potential danger to the patient is an overdose of an opiate determined by the microprocessor from the patient's blood oxygen level;
the substance is a nalaxone opioid inverse agonist; and
the administration device is operable to administer an amount of the nalaxone opioid inverse agonist determined by the microprocessor to be appropriate according to the amount of the opiate overdose, and the nalaxone opioid inverse agonist is administered by one of intravenous injection, intramuscular injection, and as a nasal spray.

6. A treatment administration unit as in claim 1 further comprising a user interface in the housing, wherein the user interface includes a visual display and a speaker and the wireless communication device includes at least one of a wireless Internet connection and cellular telephone circuitry for receiving at least one of video and audio signals from personnel associated with a healthcare facility.

7. A treatment administration unit as in claim 6, wherein the microprocessor includes an emergency contact index of at least one individual to be notified when the medical condition presents a potential danger to the patient, and the wireless communication device automatically notifies the individual of the patient's medical condition and the healthcare facility that has been contacted.

8. A treatment administration unit as in claim 1, wherein the healthcare facility index includes information relating to the capabilities of the indexed healthcare facilities relative to the patient's medical condition and the microprocessor is operable to select the healthcare facility to contact based on the capabilities of healthcare facilities near to the unit's location.

9. A treatment administration unit as in claim 1, wherein the microprocessor is operable to select the nearest healthcare facility to contact based on its proximity to the unit's location.

10. A treatment administration unit as in claim 1, wherein the circuitry for detecting the location of the unit comprises a GPS system.

11. A treatment administration unit as in claim 1, wherein the first predetermined time is shorter than the second predetermined time.

12. A treatment administration unit as in claim 11, wherein the first predetermined time is about five seconds and the second predetermined time is between 10 seconds and one minute.

13. A treatment administration unit as in claim 1, wherein the proximity sensor is a contact sensor for generating the sensing signal when the unit is in contact with the patient's skin.

14. A treatment administration unit as in claim 1, further comprising a user interface including at least one of a display and a speaker in the housing for communicating information to a user of the unit relating to the operation thereof, wherein:
the microprocessor is operable in response to the determination of the medical condition presenting a potential danger to the patient to determine a dosage of the substance to be administered to the patient for treating the medical condition and to inform the user of the dosage via the user interface by at least one of displaying the dosage on the user interface display and announcing the dosage over the user interface speaker;
the microprocessor is operable in response to the start signal to instruct the user via at least the user interface speaker to orient the unit relative to the patient for generation of a sensing signal and to inform the user of the predetermined time after generation of the start signal until the substance will be introduced into the patient by the administration device; and
the microprocessor is operable to provide a second-by-second audible countdown over the user interface speaker of the time elapsed from generation of the start signal.

15. A treatment administration unit as in claim 14, wherein the microprocessor is operable to effect at least one of the following when the first predetermined time elapses before generation of the sensing signal: (i) cause the user interface to again instruct the user to orient the unit relative to the patient for generation of a sensing signal, and (ii) cause the wireless communication device to notify a healthcare facility of the existence of the medical condition presenting a potential danger to the patient and the location of the unit.

16. A treatment administration unit as in claim 14, wherein the user interface includes a manual input device for permitting the user to determine a different dosage of the substance from the dosage determined by the microprocessor and the operation of the administration device can be enabled only after the dosage has been determined.

17. A treatment administration unit as in claim 1, wherein the administration device is enabled manually by a user of the unit.

18. A treatment administration unit as in claim 1, further comprising a user interface for receiving operational commands from a user of the unit, wherein:
a dosage of the substance to be administered to the patient is determined by one of: (i) the microprocessor in accordance with the stored treatment protocol for the patient, and (ii) a dosage input using the user interface; and the microprocessor is operable after determination of the dosage to actuate a motor in the housing to enable the operation of the administration device.

19. A treatment administration unit as in claim 1, wherein the second predetermined time is between 10 seconds and one minute.

20. A treatment administration unit as in claim 1, wherein:
the property is the patient's blood glucose level;
the medical condition presenting a potential danger to the patient is hyperglycemia determined by the microprocessor from the patient's blood glucose level;
the substance is insulin; and
the administration device is operable to administer an amount of the insulin determined by the microprocessor to be appropriate according to the patient's blood glucose level and the insulin is administered by injection using a hypodermic syringe.

21. A treatment administration unit as in claim 20, wherein the biological sample is the blood of the patient.

22. A treatment administration unit as in claim 1, further comprising a replacement second administration module accepted by the unit and containing a second substance effective to treat a medical condition of the patient.

23. A blood glucose testing unit comprising:
a housing of a size suitable for transport in a handbag or clothing pocket;
a sampling module in the housing operable to take a biological sample from a patient and determine the patient's blood glucose level from the biological sample;
a microprocessor in the housing for operating the sampling module;
an insulin administration unit in the housing, the administration unit including (i) a container for insulin and (ii) an administration device operable to administer the insulin internally of the patient from the container under the control of the microprocessor, wherein a start signal is generated when operation of the administration device is enabled;
a proximity sensor for generating a sensing signal when the unit is oriented relative to the patient for operation of the administration device;
a user interface in the housing under the control of the microprocessor, the user interface including (i) at least one of a display and a speaker for communicating information to a user of the unit, and (ii) an input device for accepting an input from the user;
a wireless communication device in the housing and under the control of the microprocessor; and
circuitry in the housing for detecting the location of the unit, wherein:
the microprocessor includes a treatment protocol memory for an individual patient that stores parameters for determining when the patient's blood glucose level indicates a hypoglycemic or hyperglycemic condition of potential danger to the patient and a healthcare facility index with geographical locations and contact information for a plurality of healthcare facilities,
the microprocessor is operable to cause the user interface to notify the user that the patient's hypoglycemic condition presents a potential danger,
the unit includes timer circuitry for measuring a time elapsed after the notification that the patient's hypoglycemic condition presents a potential danger, for measuring the time elapsed from the determination by the microprocessor that the patient's hyperglycemic condition presents a potential danger, and for measuring a time elapsed from generation of the start signal,
the microprocessor is operable to determine from the location of the unit and the healthcare facility index a location a healthcare facility that can treat the patient,
the wireless communication device automatically notifies a healthcare facility of the existence of a patient with a potentially dangerous level of hypoglycemia and the location of the unit in the absence of an input via the user interface acknowledging the notification before the elapse of a first predetermined time,
the microprocessor automatically operates the administration device to introduce the insulin internally of the patient when the sensing signal is generated prior to the elapse of a second predetermined time after generation of the start signal, and
the wireless communication device automatically notifies a healthcare facility of the existence of a patient with a potentially dangerous level of hyperglycemia and the location of the unit in the absence of a start signal before the elapse of a third predetermined time.

24. A treatment administration unit as in claim 23, wherein the microprocessor is operable to effect at least one of the following when the second predetermined time elapses before generation of the sensing signal: (i) cause the user interface to again instruct the user to orient the unit relative to the patient for generation of a sensing signal, and (ii) cause the wireless communication device to notify a healthcare facility of the existence of the hyperglycemic condition presenting a potential danger to the patient and the location of the unit.

25. A blood glucose testing unit as in claim 23, wherein the biological sample is the blood of the patient.

26. A blood glucose testing unit as in claim 23, wherein the microprocessor is operable when the patient's blood glucose level indicates a hypoglycemic condition to cause the user interface to provide instructions for the patient to ingest at least one blood glucose containing substance.

27. A blood glucose testing unit as in claim 23, wherein the second predetermined time is shorter than the third predetermined time.

28. A blood glucose testing unit as in 27, wherein the second predetermined time is about five seconds and the third predetermined time is between 10 seconds and one minute.

* * * * *